(12) United States Patent
Pulst et al.

(10) Patent No.: US 6,960,650 B2
(45) Date of Patent: Nov. 1, 2005

(54) SCHWANNOMIN-BINDING PROTEINS

(75) Inventors: Stefan M. Pulst, Los Angeles, CA (US); Daniel R. Scoles, Los Angeles, CA (US)

(73) Assignee: Cedars-Sinai Medical Center, Los Angeles, CA (US)

( * ) Notice: Subject to any disclaimer, the term of this patent is extended or adjusted under 35 U.S.C. 154(b) by 0 days.

(21) Appl. No.: 10/117,604

(22) Filed: Apr. 4, 2002

(65) Prior Publication Data

US 2002/0168672 A1 Nov. 14, 2002

Related U.S. Application Data

(62) Division of application No. 08/971,089, filed on Nov. 14, 1997, now Pat. No. 6,376,174.
(60) Provisional application No. 60/030,987, filed on Nov. 15, 1996.

(51) Int. Cl.$^7$ .................. C07H 21/02; C07H 21/04; C07K 14/435
(52) U.S. Cl. ............. 530/350; 530/395; 530/397; 536/23.1; 536/23.5
(58) Field of Search .................. 530/350, 395, 530/397; 536/23.1, 23.5, 231

(56) References Cited

PUBLICATIONS

Scoles et al. American Journal of Human Genetics. (1996) 59(supplement 4) Abstract A5.*
Trofatter et al. Cell. (1993) 72: 791–800.*
Takeshima et al. Oncogene (1994) 9: 2135–2144.*
Chang et al., "Cloning of a Portion of the Chromosomal Gene and cDNA for Human β–Fodrin, the Nonerythroid Form of β–Spectrin," *Genomics*, 17:287–293 (1993).
Dorsey et al., "Merlin Protein—Protein Interactions Revealed by the Two Hybrid System," *Molecular Biology of the Cell*, 7:23A, Abstract #137 (1996).
Database Accession No. AAT80430 XP002270087 "WO97/04104".
Database Accession No. AAT20293 XP002270088 "HUMGS01442".
Database Accession No. AAT41047 XP002270089 "HUMGS01442 derived sense primer".
Database Accession No. I32121 XP002270090 "Sequence 11".
Database Accessioin No. AAT41048 XP002270092 "HUMGS01442 derived anti–sense primer".
Asano, et al., "Conservation and Diversity of Eukaryotic Translation Initiation Factor eIF3," *J. Biol. Chem.*, 272(2):1101–1109 (1997).
Discher et al., "Mechanochemistry of the Alternatively Spliced Spectrin–Actin Binding Domain in Membrane Skeletal Protein 4.1," *J. Biol. Chem.*, 268(10):7186–7195 (1993).
Subrahmanyam et al., "Phosphorylation of protein 4.1 on tyrosine–418 modulates its function in vitro," *Proc. Natl. Acad. Sci. USA*, 88:5222–5226 (1991).
Takeshima et al., "Detection of cellular proteins that interact with the NF2 tumor suppressor gene product," *Oncogene*, 9:2135–2144 (1994).
Trofatter et al., "A Novel Moesin–, Ezrin–, Radixin–like Gene Is a Candidate for the Neurofibromatosis 2 Tumor Suppressor," *Cell*, 72:791–800 (1993).
Fields and Song, "A novel genetic system to detect protein—protein interactions," *Nature*, 340:245–246 (1989).
Fox et al., "On the Role of the Platelet Membrane Skeleton in Mediating Signal Transduction," *J. Biol. Chem.*, 268(34):25973–25984 (1993).
Nelson et al., "Identification of a Membrane–Cytoskeletal Complex Containing the Cell Adhesion Molecule Uvomorulin (E–Cadherin), Ankyrin, and Fodrin in Madin–Darby Canine Kidney Epithelial Cells," *J. Cell. Biol.*, 110:349–357 (1990).
Paul et al., "Characterization of Fodrin Interaction with the NF2 Tumor Suppressor Gene Product Schwannomin (merlin) and Varying Strengths of Protein Binding that Correlate with NF2 Patient Phenotypes," *Neurology*, 48(3)(suppl.2):A393–A394 (1997).
Rouleau et al., "Alteration in a new gene encoding a putative membrane–organizing protein causes neuro–fibromatosis type 2," *Nature*, 363:515–521 (1993).
Sainz et al., "Mutations of the neurofibroatosis type 2 gene and lack of the gene product in vestibular schwannomas," *Human Mol. Genet.*, 3(6):885–891 (1994).
Scoles et al., "The neurofibromatosis 2 gene product schwannomin interacts with βII–spectrin," *Am. J. of Human Genetics.*, 59(4 suppl.) Abstract A5 (1996).
Scoles et al., "Identification and Characterization of Interaction Between the NF2 Gene Product Schwannomin and βII–Spectrin," *Mol. Biol. of the Cell*, 7(suppl.):386A (1996).
Wei et al., "Molecular cloning and functional analysis of a human DNA encoding an *Escherichia coli* AlkB homolog, a protein involved in DNA alkylation damage repair," *Nucleic Acids Research*, 24: 931–937 (1996).
*USB Catalog*, Molecular Biology Reagents, p. 166 (1990).
Adams et al., GenBank Accession No.: AA314857.
Adams et al., GenBank Accession No.: AA305985.
Asano et al., GenBank Accession No.: U46025.

* cited by examiner

*Primary Examiner*—Carla J. Myers
(74) *Attorney, Agent, or Firm*—McDermott Will & Emery

(57) ABSTRACT

In accordance with the present invention, there are provided novel Schwannomin-Binding-Proteins (SBPs). Nucleic acid sequences encoding such proteins and assays employing same are also disclosed. The invention SBPs can be employed in a variety of ways, for example, for the production of anti-SBP antibodies thereto, in therapeutic compositions and methods employing such proteins and/or antibodies. Also provided are transgenic non-human mammals that express the invention protein.

3 Claims, 2 Drawing Sheets

SEQUENCE LISTING (1) GENERAL INFORMATION:

(iii) NUMBER OF SEQUENCES: 10

(2) INFORMATION FOR SEQ ID NO: 1:

(i) SEQUENCE CHARACTERISTICS:
      (A) LENGTH: 1298 base pairs
      (B) TYPE: nucleic acid
      (C) STRANDEDNESS: both
      (D) TOPOLOGY: both (ii) MOLECULE TYPE: cDNA (ix) FEATURE:
    (A) NAME/KEY: CDS
    (B) LOCATION: 2..193

(xi) SEQUENCE DESCRIPTION: SEQ ID NO: 1:

```
G GAA GGG AGG AAG AGA GAG AGG AAG AAA GAG AAA GAG AAG AAA GAA          46
  Glu Gly Arg Lys Arg Glu Arg Lys Lys Glu Lys Glu Lys Lys Glu
  1               5                   10                  15

AAA AAG AAA AAG AAA GAA ACA AAG AAA GAA GAG AGA AAG AGA AAG AAA        94
Lys Lys Lys Lys Lys Glu Thr Lys Lys Glu Glu Arg Lys Arg Lys Lys
                20                  25                  30

GAG AAA GAA AAA AAA GAA AGA GAA AGA AAA GAA AAA GAA AAG AGA AAA        142
Glu Lys Glu Lys Lys Glu Arg Glu Arg Lys Glu Lys Glu Lys Arg Lys
                35                  40                  45

GGA AAG AGA ATT ACA TAT TAC TTC TCT GGG CCA GAT TCA GCC CTC TGT        190
Gly Lys Arg Ile Thr Tyr Tyr Phe Ser Gly Pro Asp Ser Ala Leu Cys
                50                  55                  60

TAAGTTCCAG GAATTGGGCC AGTTTTACAA ACTGCATAAC CATGAGCAGA GGCCAAACTC      250

CCATTACCTG ATCTCTTGGT GTATCGCCTT TCTTTGAGGT ATTCATCATG CTGTTTTAAA      310

ATTATGTCTT TTCTCTTTTT GTCATCACTG ATTTAGAAAA ACCTTACTCT GTTTCCTTAC      370

CTATCCACAC TTTCTATTCG TGTTACTTTT TCCTCCAGCC CAATCTTGCT TCCATCAAAT      430

TTAATGTGTA ATACTATCAT AGCCATTATC ATGCTATTTT CTGTATATAG TGTTTGTGTT      490

TTCCAAGGGG TGAAAACACT GTAAAGTTAC ACTACTTCTC AATCCATCAA ATTTACTGTT      550

AGTTATCTAC CTAAGATAAA TGAAAACATA TATCCACACA CACTGGCCCT ATAGTGGAAA      610

CATCTAATCA TGTGTCACCT GGTGAATGAA TTCACAAAAT TAGAGAACTC TTATGTATGA      670

AGCTATGTAC CTGATTTTCT TACCTAAGTT ATTTGAAAGC ACAAACACAC TTTTTTGTGT      730

ATATTTTAGT TGCGTGCCAT GCCTGGGCTC AGANNNNNNN NNNNNNNNTC AGTGAAGTGA      790

AACATTCAAA AACTGATTTA TGGCAATGGT TTCAAAGCTT GGTAAATTTA CTAAAATATC      850

ATTGAATTCT AACAACTTGA AATGGATGAA TTATATGATA TGTAAAACAT GCCTCAGTTA      910

AGTTACTTTT TGAAACTTAG ATTACTTGTC TTTTCCTTAT TGAGGTTTGA ACCAGCAGCC      970

CAAGATNTGG CCTATGGAAG TTTTGATGCT CATATNTCTA CCATTCTGTA CTCAACATTT      1030

TCCCCTATTT TAACAAAAGC ATTAGTTATT ACTCATTTGT TTATAATAAG AATATAGAGG      1090

CCTTATTTCC AATTTGATAG ATATTTTGGT TACTATTAAA AAGTCAGACA TGATTGTAAT      1150

ATAGTTGCAT AAATACAGTT ATTTTTTTTA ACTAGTCACA ATTCATTTCA TGTTTTCCCG      1210

TTGTTGAAAA AAAGTTTTT TTGGGGCAAT CCCTAAAATA AAAGATTNTG TAATAAAATG       1270

AAGTTTGCAA AAAAAAAAAA AAAAAAAA                                        1298
```

(2) INFORMATION FOR SEQ ID NO: 2:

(i) SEQUENCE CHARACTERISTICS:
        (A) LENGTH: 63 amino acids
        (B) TYPE: amino acid
        (D) TOPOLOGY: linear (ii) MOLECULE TYPE: protein (xi) SEQUENCE DESCRIPTION: SEQ ID NO: 2:

```
Glu Gly Arg Lys Arg Glu Arg Lys Lys Glu Lys Glu Lys Lys Glu
1               5                   10                  15

Lys Lys Lys Lys Glu Thr Lys Lys Glu Glu Arg Lys Arg Lys Lys Glu
```

```
                    20                    25                    30
Lys Glu Lys Glu Arg Glu Arg Lys Glu Lys Glu Lys Arg Lys Gly
        35                    40                    45

Lys Arg Ile Thr Tyr Tyr Phe Ser Gly Pro Asp Ser Ala Leu Cys
        50                    55                    60

(2) INFORMATION FOR SEQ ID NO: 3:

(i) SEQUENCE CHARACTERISTICS:
        (A) LENGTH: 2854 base pairs
        (B) TYPE: nucleic acid
        (C) STRANDEDNESS: both
        (D) TOPOLOGY: both (ii) MOLECULE TYPE: cDNA (ix) FEATURE:
        (A) NAME/KEY: CDS
        (B) LOCATION: 45..2786

(xi) SEQUENCE DESCRIPTION: SEQ ID NO: 3:

CGCGGGCTCA GCTGGACCGG CCGTAGCACC TCCGCGCCGT CGCC ATG TCG CGG TTT       56
                                                Met Ser Arg Phe
                                                  1

TTC ACC ACC GGT TCG GAC AGC GAG TCC GAG TCG TCC TTG TCC GGG GAG      104
Phe Thr Thr Gly Ser Asp Ser Glu Ser Glu Ser Ser Leu Ser Gly Glu
  5                  10                  15                  20

GAG CTC GTC ACC AAA CCT GTC GGA GGC AAC TAT GGC AAA CAG CCA TTG      152
Glu Leu Val Thr Lys Pro Val Gly Gly Asn Tyr Gly Lys Gln Pro Leu
                 25                  30                  35

TTG CTG AGC GAG GAT GAA GAA GAT ACC AAG AGA GTT GTC CGC AGT GCC      200
Leu Leu Ser Glu Asp Glu Glu Asp Thr Lys Arg Val Val Arg Ser Ala
             40                  45                  50

AAG GAC AAG AGG TTT GAG GAG CTG ACC AAC CTT ATC CGG ACC ATC CGT      248
Lys Asp Lys Arg Phe Glu Glu Leu Thr Asn Leu Ile Arg Thr Ile Arg
         55                  60                  65

AAT GCC ATG AAG ATT CGT GAT GTC ACC AAG TGC CTG GAA GAG TTT GAG      296
Asn Ala Met Lys Ile Arg Asp Val Thr Lys Cys Leu Glu Glu Phe Glu
 70                  75                  80

CTC CTG GGA AAA GCA TAT GGG AAG GCC AAA AGC ATT GTG GAC AAA GAA      344
Leu Leu Gly Lys Ala Tyr Gly Lys Ala Lys Ser Ile Val Asp Lys Glu
 85                  90                  95                 100

GGT GTC CCC CGG TTC TAT ATC CGC ATC CTG GCT GAC CTA GAG GAC TAT      392
Gly Val Pro Arg Phe Tyr Ile Arg Ile Leu Ala Asp Leu Glu Asp Tyr
                105                 110                 115

CTT AAT GAG CTT TGG GAA GAT AAG GAA GGG AAG AAG AAG ATG AAC AAG      440
Leu Asn Glu Leu Trp Glu Asp Lys Glu Gly Lys Lys Lys Met Asn Lys
            120                 125                 130

AAC AAT GCC AAG GCT CTG AGC ACC TTG CGT CAG AAG ATC CGA AAA TAC      488
Asn Asn Ala Lys Ala Leu Ser Thr Leu Arg Gln Lys Ile Arg Lys Tyr
        135                 140                 145

AAC CGT GAT TTC GAG TCC CAT ATC ACA AGC TAC AAG CAG AAC CCC GAG      536
Asn Arg Asp Phe Glu Ser His Ile Thr Ser Tyr Lys Gln Asn Pro Glu
    150                 155                 160

CAG TCT GCG GAT GAA GAT GCT GAG AAA AAT GAG GAG GAT TCA GAA GGC      584
Gln Ser Ala Asp Glu Asp Ala Glu Lys Asn Glu Glu Asp Ser Glu Gly
165                 170                 175                 180

TCT TCA GAT GAG GAT GAG GAT GAG GAC GGA GTC AGT GCT GCA ACT TTC      632
Ser Ser Asp Glu Asp Glu Asp Glu Asp Gly Val Ser Ala Ala Thr Phe
                185                 190                 195

TTG AAG AAG AAA TCA GAA GCT CCT TCT GGG GAG AGT CGC AAG TTC CTC      680
Leu Lys Lys Lys Ser Glu Ala Pro Ser Gly Glu Ser Arg Lys Phe Leu
```

```
            200                 205                 210
AAA AAG ATG GAT GAT GAA GAT GAG GAC TCA GAA GAT TCC GAA GAT GAT     728
Lys Lys Met Asp Asp Glu Asp Glu Asp Ser Glu Asp Ser Glu Asp Asp
            215                 220                 225

GAA GAC TGG GAC ACA GGT TCC ACA TCT TCC GAT TCC GAC TCA GAG GAG     776
Glu Asp Trp Asp Thr Gly Ser Thr Ser Ser Asp Ser Asp Ser Glu Glu
            230                 235                 240

GAA GAA GGG AAA CAA ACC GCG CTG GCC TCA AGA TTT CTT AAA AAG GCA     824
Glu Glu Gly Lys Gln Thr Ala Leu Ala Ser Arg Phe Leu Lys Lys Ala
245                 250                 255                 260

CCC ACC ACA GAT GAG GAC AAG AAG GCA GCC GAG AAG AAA CGG GAG GAC     872
Pro Thr Thr Asp Glu Asp Lys Lys Ala Ala Glu Lys Lys Arg Glu Asp
            265                 270                 275

AAA GCT AAG AAG AAG CAC GAC AGG AAA TCC AAG CGC CTG GAT GAG GAG     920
Lys Ala Lys Lys Lys His Asp Arg Lys Ser Lys Arg Leu Asp Glu Glu
            280                 285                 290

GAG GAG GAC AAT GAA GGC GGG GAG TGG GAA AGG GTC CGG GGC GGA GTG     968
Glu Glu Asp Asn Glu Gly Gly Glu Trp Glu Arg Val Arg Gly Gly Val
            295                 300                 305

CCG TTG GTT AAG GAG AAG CCA AAA ATG TTT GCC AAG GGA ACT GAG ATC    1016
Pro Leu Val Lys Glu Lys Pro Lys Met Phe Ala Lys Gly Thr Glu Ile
            310                 315                 320

ACC CAT GCT GTT GTT ATC AAG AAA CTG AAT GAG ATC CTA CAG GCA CGA    1064
Thr His Ala Val Val Ile Lys Lys Leu Asn Glu Ile Leu Gln Ala Arg
325                 330                 335                 340

GGC AAG AAG GGA ACT GAT CGT GCT GCC CAG ATT GAG CTG CTG CAA CTG    1112
Gly Lys Lys Gly Thr Asp Arg Ala Ala Gln Ile Glu Leu Leu Gln Leu
            345                 350                 355

CTG GTT CAG ATT GCA GCG GAA AAC AAC CTG GGA GAG GGC GTC ATT GTC    1160
Leu Val Gln Ile Ala Ala Glu Asn Asn Leu Gly Glu Gly Val Ile Val
            360                 365                 370

AAG ATC AAG TTC AAT ATC ATC GCC TCT CTC TAT GAC TAC AAC CCC AAC    1208
Lys Ile Lys Phe Asn Ile Ile Ala Ser Leu Tyr Asp Tyr Asn Pro Asn
            375                 380                 385

CTG GCA ACC TAC ATG AAG CCA GAG ATG TGG GGG AAG TGC CTG GAC TGC    1256
Leu Ala Thr Tyr Met Lys Pro Glu Met Trp Gly Lys Cys Leu Asp Cys
            390                 395                 400

ATC AAT GAG CTG ATG GAT ATC CTG TTT GCA AAT CCC AAC ATT TTT GTT    1304
Ile Asn Glu Leu Met Asp Ile Leu Phe Ala Asn Pro Asn Ile Phe Val
405                 410                 415                 420

GGA GAG AAT ATT CTG GAA GAG AGT GAG AAC CTG CAC AAC GCT GAC CAG    1352
Gly Glu Asn Ile Leu Glu Glu Ser Glu Asn Leu His Asn Ala Asp Gln
            425                 430                 435

CCA CTG CGT GTC CGT GGC TGC ATC CTA ACT CTG GTG GAA CGA ATG GAT    1400
Pro Leu Arg Val Arg Gly Cys Ile Leu Thr Leu Val Glu Arg Met Asp
            440                 445                 450

GAA GAA TTT ACC AAA ATA ATG CAA AAT ACT GAC CCT CAC TCC CAA GAG    1448
Glu Glu Phe Thr Lys Ile Met Gln Asn Thr Asp Pro His Ser Gln Glu
            455                 460                 465

TAC GTG GAG CAC TTG AAG GAT GAG GCC CAG GTG TGT GCC ATC ATC GAG    1496
Tyr Val Glu His Leu Lys Asp Glu Ala Gln Val Cys Ala Ile Ile Glu
            470                 475                 480

CGT GTG CAG CGC TAC CTG GAG GAG AAG GGC ACT ACC GAG GAG GTC TGC    1544
Arg Val Gln Arg Tyr Leu Glu Glu Lys Gly Thr Thr Glu Glu Val Cys
485                 490                 495                 500

CGC ATC TAC CTG CTG CGC ATC CTG CAC ACC TAC TAC AAG TTT GAT TAC    1592
Arg Ile Tyr Leu Leu Arg Ile Leu His Thr Tyr Tyr Lys Phe Asp Tyr
            505                 510                 515

AAG GCC CAT CAG CGA CAG CTG ACC CCG CCT GAG GGC TCC TCA AAG TCT    1640
```

-continued

```
                Lys Ala His Gln Arg Gln Leu Thr Pro Pro Glu Gly Ser Ser Lys Ser
                                520                 525                 530

GAG CAA GAC CAG GCA GAA AAT GAG GGC GAG GAC TCG GCT GTG TTG ATG             1688
Glu Gln Asp Gln Ala Glu Asn Glu Gly Glu Asp Ser Ala Val Leu Met
            535                 540                 545

GAG AGA CTG TGC AAG TAC ATC TAC GCC AAG GAC CGC ACA GAC CGG ATC             1736
Glu Arg Leu Cys Lys Tyr Ile Tyr Ala Lys Asp Arg Thr Asp Arg Ile
550                 555                 560

CGC ACA TGT GCC ATC CTC TGC CAC ATC TAC CAC CAT GCT CTG CAC TCG             1784
Arg Thr Cys Ala Ile Leu Cys His Ile Tyr His His Ala Leu His Ser
565                 570                 575                 580

CGC TGG TAC CAG GCC CGC GAC CTC ATG CTC ATG AGC CAC TTG CAG GAC             1832
Arg Trp Tyr Gln Ala Arg Asp Leu Met Leu Met Ser His Leu Gln Asp
                585                 590                 595

AAC ATT CAG CAT GCA GAC CCG CCA GTG CAG ATC CTT TAC AAC CGC ACC             1880
Asn Ile Gln His Ala Asp Pro Pro Val Gln Ile Leu Tyr Asn Arg Thr
            600                 605                 610

ATG GTG CAG CTG GGC ATC TGT GCC TTC CGC CAA GGC CTG ACC AAG GAC             1928
Met Val Gln Leu Gly Ile Cys Ala Phe Arg Gln Gly Leu Thr Lys Asp
            615                 620                 625

GCA CAC AAC GCC CTG CTG GAC ATC CAG TCG AGT GGC CGA GCC AAG GAG             1976
Ala His Asn Ala Leu Leu Asp Ile Gln Ser Ser Gly Arg Ala Lys Glu
630                 635                 640

CTT CTG GGC CAG GGC CTG CTG CTG CGC AGC CTG CAG GAG CGC AAC CAG             2024
Leu Leu Gly Gln Gly Leu Leu Leu Arg Ser Leu Gln Glu Arg Asn Gln
645                 650                 655                 660

GAG CAG GAG AAG GTG GAG CGG CGC CGT CAG GTC CCC TTC CAC CTG CAC             2072
Glu Gln Glu Lys Val Glu Arg Arg Arg Gln Val Pro Phe His Leu His
                665                 670                 675

ATC AAC CTG GAG CTG CTG GAG TGT GTC TAC CTG GTG TCT GCC ATG CTC             2120
Ile Asn Leu Glu Leu Leu Glu Cys Val Tyr Leu Val Ser Ala Met Leu
            680                 685                 690

CTG GAG ATC CCC TAC ATG GCC GCC CAT GAG AGC GAT GCC CGC CGA CGC             2168
Leu Glu Ile Pro Tyr Met Ala Ala His Glu Ser Asp Ala Arg Arg Arg
            695                 700                 705

ATG ATC AGC AAG CAG TTC CAC CAC CAG CTG CGC GTG GGC GAG CGA CAG             2216
Met Ile Ser Lys Gln Phe His His Gln Leu Arg Val Gly Glu Arg Gln
710                 715                 720

CCC CTG CTG GGT CCC CCT GAG TCC ATG CGG GAA CAT GTG GTC GCT GCC             2264
Pro Leu Leu Gly Pro Pro Glu Ser Met Arg Glu His Val Val Ala Ala
725                 730                 735                 740

TCC AAG GCC ATG AAG ATG GGT GAC TGG AAG ACC TGT CAC AGT TTT ATC             2312
Ser Lys Ala Met Lys Met Gly Asp Trp Lys Thr Cys His Ser Phe Ile
                745                 750                 755

ATC AAT GAG AAG ATG AAT GGG AAA GTG TGG GAC CTT TTC CCC GAG GCT             2360
Ile Asn Glu Lys Met Asn Gly Lys Val Trp Asp Leu Phe Pro Glu Ala
            760                 765                 770

GAC AAA GTC CGC ACC ATG CTG GTT AGG AAG ATC CAG GAA GAG TCA CTG             2408
Asp Lys Val Arg Thr Met Leu Val Arg Lys Ile Gln Glu Glu Ser Leu
            775                 780                 785

AGG ACC TAC CTC TTC ACC TAC AGC AGT GTC TAT GAC TCC ATC AGC ATG             2456
Arg Thr Tyr Leu Phe Thr Tyr Ser Ser Val Tyr Asp Ser Ile Ser Met
790                 795                 800

GAG ACG CTG TCA GAC ATG TTT GAG CTG GAT CTG CCC ACT GTG CAC TCC             2504
Glu Thr Leu Ser Asp Met Phe Glu Leu Asp Leu Pro Thr Val His Ser
805                 810                 815                 820

ATC ATC AGC AAA ATG ATC ATT AAT GAG GAG CTG ATG GCC TCC CTG GAC             2552
Ile Ile Ser Lys Met Ile Ile Asn Glu Glu Leu Met Ala Ser Leu Asp
                825                 830                 835
```

```
CAG CCA ACA CAG ACA GTG GTG ATG CAC CGC ACT GAG CCC ACT GCC CAG      2600
Gln Pro Thr Gln Thr Val Val Met His Arg Thr Glu Pro Thr Ala Gln
            840                 845                 850

CAG AAC CTG GCT CTG CAG CTG GCC GAG AAG CTG GGC AGC CTG GTG GAG      2648
Gln Asn Leu Ala Leu Gln Leu Ala Glu Lys Leu Gly Ser Leu Val Glu
        855                 860                 865

AAC AAC GAA CGG GTG TTT GAC CAC AAG CAG GGC ACC TAC GGG GGC TAC      2696
Asn Asn Glu Arg Val Phe Asp His Lys Gln Gly Thr Tyr Gly Gly Tyr
    870                 875                 880

TTC CGA GAC CAG AAG GAC GGC TAC CGC AAA AAC GAG GGC TAC ATG CGC      2744
Phe Arg Asp Gln Lys Asp Gly Tyr Arg Lys Asn Glu Gly Tyr Met Arg
885                 890                 895                 900

CGC GGT GGC TAC CGC CAG CAG CAG TCT CAG ACG GCC TAC TGAGCTCTCC       2793
Arg Gly Gly Tyr Arg Gln Gln Gln Ser Gln Thr Ala Tyr
                905                 910

ACTCTGTTTC CGCCTGGGC CATCCAACCT TGAAGTCCTA AACCACACCT CAGTCACTAA     2853

A                                                                    2854

(2) INFORMATION FOR SEQ ID NO: 4:

(i) SEQUENCE CHARACTERISTICS:
        (A) LENGTH: 913 amino acids
        (B) TYPE: amino acid
        (D) TOPOLOGY: linear (ii) MOLECULE TYPE: protein (xi) SEQUENCE DESCRIPTION: SEQ ID NO: 4:

Met Ser Arg Phe Phe Thr Thr Gly Ser Asp Ser Glu Ser Glu Ser Ser
1               5                   10                  15

Leu Ser Gly Glu Glu Leu Val Thr Lys Pro Val Gly Gly Asn Tyr Gly
            20                  25                  30

Lys Gln Pro Leu Leu Leu Ser Glu Asp Glu Asp Thr Lys Arg Val
        35                  40                  45

Val Arg Ser Ala Lys Asp Lys Arg Phe Glu Glu Leu Thr Asn Leu Ile
    50                  55                  60

Arg Thr Ile Arg Asn Ala Met Lys Ile Arg Asp Val Thr Lys Cys Leu
65                  70                  75                  80

Glu Glu Phe Glu Leu Leu Gly Lys Ala Tyr Gly Lys Ala Lys Ser Ile
                85                  90                  95

Val Asp Lys Glu Gly Val Pro Arg Phe Tyr Ile Arg Ile Leu Ala Asp
            100                 105                 110

Leu Glu Asp Tyr Leu Asn Glu Leu Trp Glu Asp Lys Glu Gly Lys Lys
        115                 120                 125

Lys Met Asn Lys Asn Ala Lys Ala Leu Ser Thr Leu Arg Gln Lys
    130                 135                 140

Ile Arg Lys Tyr Asn Arg Asp Phe Glu Ser His Ile Thr Ser Tyr Lys
145                 150                 155                 160

Gln Asn Pro Glu Gln Ser Ala Asp Glu Asp Ala Glu Lys Asn Glu Glu
                165                 170                 175

Asp Ser Glu Gly Ser Ser Asp Glu Glu Asp Glu Asp Gly Val Ser
            180                 185                 190

Ala Ala Thr Phe Leu Lys Lys Lys Ser Glu Ala Pro Ser Gly Glu Ser
        195                 200                 205

Arg Lys Phe Leu Lys Lys Met Asp Asp Glu Asp Glu Asp Ser Glu Asp
    210                 215                 220

Ser Glu Asp Asp Glu Asp Trp Asp Thr Gly Ser Thr Ser Ser Asp Ser
```

```
            225                 230                 235                 240
Asp Ser Glu Glu Glu Gly Lys Gln Thr Ala Leu Ala Ser Arg Phe
                245                 250                 255
Leu Lys Lys Ala Pro Thr Thr Asp Glu Asp Lys Lys Ala Ala Glu Lys
                260                 265                 270
Lys Arg Glu Asp Lys Ala Lys Lys His Asp Arg Lys Ser Lys Arg
                275                 280                 285
Leu Asp Glu Glu Glu Asp Asn Glu Gly Glu Trp Glu Arg Val
        290                 295                 300
Arg Gly Gly Val Pro Leu Val Lys Glu Lys Pro Lys Met Phe Ala Lys
305                 310                 315                 320
Gly Thr Glu Ile Thr His Ala Val Val Ile Lys Lys Leu Asn Glu Ile
                325                 330                 335
Leu Gln Ala Arg Gly Lys Lys Gly Thr Asp Arg Ala Ala Gln Ile Glu
                340                 345                 350
Leu Leu Gln Leu Leu Val Gln Ile Ala Ala Glu Asn Asn Leu Gly Glu
            355                 360                 365
Gly Val Ile Val Lys Ile Lys Phe Asn Ile Ile Ala Ser Leu Tyr Asp
        370                 375                 380
Tyr Asn Pro Asn Leu Ala Thr Tyr Met Lys Pro Glu Met Trp Gly Lys
385                 390                 395                 400
Cys Leu Asp Cys Ile Asn Glu Leu Met Asp Ile Leu Phe Ala Asn Pro
                405                 410                 415
Asn Ile Phe Val Gly Glu Asn Ile Leu Glu Glu Ser Glu Asn Leu His
                420                 425                 430
Asn Ala Asp Gln Pro Leu Arg Val Arg Gly Cys Ile Leu Thr Leu Val
            435                 440                 445
Glu Arg Met Asp Glu Glu Phe Thr Lys Ile Met Gln Asn Thr Asp Pro
        450                 455                 460
His Ser Gln Glu Tyr Val Glu His Leu Lys Asp Glu Ala Gln Val Cys
465                 470                 475                 480
Ala Ile Ile Glu Arg Val Gln Arg Tyr Leu Glu Glu Lys Gly Thr Thr
                485                 490                 495
Glu Glu Val Cys Arg Ile Tyr Leu Leu Arg Ile Leu His Thr Tyr Tyr
                500                 505                 510
Lys Phe Asp Tyr Lys Ala His Gln Arg Gln Leu Thr Pro Pro Glu Gly
            515                 520                 525
Ser Ser Lys Ser Glu Gln Asp Gln Ala Glu Asn Glu Gly Glu Asp Ser
        530                 535                 540
Ala Val Leu Met Glu Arg Leu Cys Lys Tyr Ile Tyr Ala Lys Asp Arg
545                 550                 555                 560
Thr Asp Arg Ile Arg Thr Cys Ala Ile Leu Cys His Ile Tyr His His
                565                 570                 575
Ala Leu His Ser Arg Trp Tyr Gln Ala Arg Asp Leu Met Leu Met Ser
            580                 585                 590
His Leu Gln Asp Asn Ile Gln His Ala Asp Pro Val Gln Ile Leu
            595                 600                 605
Tyr Asn Arg Thr Met Val Gln Leu Gly Ile Cys Ala Phe Arg Gln Gly
        610                 615                 620
Leu Thr Lys Asp Ala His Asn Ala Leu Leu Asp Ile Gln Ser Ser Gly
625                 630                 635                 640
Arg Ala Lys Glu Leu Leu Gly Gln Gly Leu Leu Leu Arg Ser Leu Gln
                645                 650                 655
```

-continued

```
Glu Arg Asn Gln Glu Gln Glu Lys Val Glu Arg Arg Gln Val Pro
        660                 665                 670

Phe His Leu His Ile Asn Leu Glu Leu Leu Glu Cys Val Tyr Leu Val
            675                 680                 685

Ser Ala Met Leu Leu Glu Ile Pro Tyr Met Ala Ala His Glu Ser Asp
        690                 695                 700

Ala Arg Arg Arg Met Ile Ser Lys Gln Phe His His Gln Leu Arg Val
705                 710                 715                 720

Gly Glu Arg Gln Pro Leu Leu Gly Pro Pro Glu Ser Met Arg Glu His
                725                 730                 735

Val Val Ala Ala Ser Lys Ala Met Lys Met Gly Asp Trp Lys Thr Cys
            740                 745                 750

His Ser Phe Ile Ile Asn Glu Lys Met Asn Gly Lys Val Trp Asp Leu
        755                 760                 765

Phe Pro Glu Ala Asp Lys Val Arg Thr Met Leu Val Arg Lys Ile Gln
    770                 775                 780

Glu Glu Ser Leu Arg Thr Tyr Leu Phe Thr Tyr Ser Ser Val Tyr Asp
785                 790                 795                 800

Ser Ile Ser Met Glu Thr Leu Ser Asp Met Phe Glu Leu Asp Leu Pro
                805                 810                 815

Thr Val His Ser Ile Ile Ser Lys Met Ile Ile Asn Glu Glu Leu Met
            820                 825                 830

Ala Ser Leu Asp Gln Pro Thr Gln Thr Val Val Met His Arg Thr Glu
        835                 840                 845

Pro Thr Ala Gln Gln Asn Leu Ala Leu Gln Leu Ala Glu Lys Leu Gly
    850                 855                 860

Ser Leu Val Glu Asn Asn Glu Arg Val Phe Asp His Lys Gln Gly Thr
865                 870                 875                 880

Tyr Gly Gly Tyr Phe Arg Asp Gln Lys Asp Gly Tyr Arg Lys Asn Glu
                885                 890                 895

Gly Tyr Met Arg Arg Gly Gly Tyr Arg Gln Gln Gln Ser Gln Thr Ala
            900                 905                 910

Tyr
```

(2) INFORMATION FOR SEQ ID NO: 5:

(i) SEQUENCE CHARACTERISTICS:
        (A) LENGTH: 2665 base pairs
        (B) TYPE: nucleic acid
        (C) STRANDEDNESS: both
        (D) TOPOLOGY: both (ii) MOLECULE TYPE: cDNA (ix) FEATURE:
        (A) NAME/KEY: CDS
        (B) LOCATION: 5..2077

(xi) SEQUENCE DESCRIPTION: SEQ ID NO: 5:

```
CGCC ATG GGG CGA GGC AGC GGC ACC TTC GAG CGT CTC CTA GAC AAG GCG      49
     Met Gly Arg Gly Ser Gly Thr Phe Glu Arg Leu Leu Asp Lys Ala
       1               5                  10                  15

ACC AGC CAG CTC CTG TTG GAG ACA GAT TGG GAG TCC ATT TTG CAG ATC      97
Thr Ser Gln Leu Leu Leu Glu Thr Asp Trp Glu Ser Ile Leu Gln Ile
             20                  25                  30

TGC GAC CTG ATC CGC CAA GGG GAC ACA CAA GCA AAA TAT GCT GTG AAT     145
Cys Asp Leu Ile Arg Gln Gly Asp Thr Gln Ala Lys Tyr Ala Val Asn
         35                  40                  45
```

| | | |
|---|---|---|
| TCC ATC AAG AAG AAA GTC AAC GAC AAG AAC CCA CAC GTC GCC TTG TAT<br>Ser Ile Lys Lys Lys Val Asn Asp Lys Asn Pro His Val Ala Leu Tyr<br>        50                      55                      60 | 193 |
| GCC CTG GAG GTC ATG GAA TCT GTG GTA AAG AAC TGT GGC CAG ACA GTT<br>Ala Leu Glu Val Met Glu Ser Val Val Lys Asn Cys Gly Gln Thr Val<br>        65                      70                      75 | 241 |
| CAT GAT GAG GTG GCC AAC AAG CAG ACC ATG GAG GAG CTG AAG GAC CTG<br>His Asp Glu Val Ala Asn Lys Gln Thr Met Glu Glu Leu Lys Asp Leu<br>80                      85                      90                      95 | 289 |
| CTG AAG AGA CAA GTG GAG GTA AAC GTC CGT AAC AAG ATC CTG TAC CTG<br>Leu Lys Arg Gln Val Glu Val Asn Val Arg Asn Lys Ile Leu Tyr Leu<br>                      100                    105                  110 | 337 |
| ATC CAG GCC TGG GCG CAT GCC TTC CGG AAC GAG CCC AAG TAC AAG GTG<br>Ile Gln Ala Trp Ala His Ala Phe Arg Asn Glu Pro Lys Tyr Lys Val<br>                      115                    120                  125 | 385 |
| GTC CAG GAC ACC TAC CAG ATC ATG AAG GTG GAG GGG CAC GTC TTT CCA<br>Val Gln Asp Thr Tyr Gln Ile Met Lys Val Glu Gly His Val Phe Pro<br>                      130                    135                  140 | 433 |
| GAA TTC AAA GAG AGC GAT GCC ATG TTT GCT GCC GAG AGA GCC CCA GAC<br>Glu Phe Lys Glu Ser Asp Ala Met Phe Ala Ala Glu Arg Ala Pro Asp<br>                      145                    150                  155 | 481 |
| TGG GTG GAC GCT GAG GAA TGC CAC CGC TGC AGG GTG CAG TTC GGG GTG<br>Trp Val Asp Ala Glu Glu Cys His Arg Cys Arg Val Gln Phe Gly Val<br>160                      165                    170                  175 | 529 |
| ATG ACC CGT AAG CAC CAC TGC CGG GCG TGT GGG CAG ATA TTC TGT GGA<br>Met Thr Arg Lys His His Cys Arg Ala Cys Gly Gln Ile Phe Cys Gly<br>                      180                    185                  190 | 577 |
| AAG TGT TCT TCC AAG TAC TCC ACC ATC CCC AAG TTT GGC ATC GAG AAG<br>Lys Cys Ser Ser Lys Tyr Ser Thr Ile Pro Lys Phe Gly Ile Glu Lys<br>                      195                    200                  205 | 625 |
| GAG GTG CGC GTG TGT GAG CCC TGC TAC GAG CAG CTG AAC AGG AAA GCG<br>Glu Val Arg Val Cys Glu Pro Cys Tyr Glu Gln Leu Asn Arg Lys Ala<br>                      210                    215                  220 | 673 |
| GAG GGA AAG GCC ACT TCC ACC ACT GAG CTG CCC CCC GAT TAC CTG ACC<br>Glu Gly Lys Ala Thr Ser Thr Thr Glu Leu Pro Pro Asp Tyr Leu Thr<br>225                      230                    235 | 721 |
| AGC CCC CTG TCT CAG CAG TCC CAG CTG CCC CCC AAG AGG GAC GAG ACG<br>Ser Pro Leu Ser Gln Gln Ser Gln Leu Pro Pro Lys Arg Asp Glu Thr<br>240                      245                    250                  255 | 769 |
| GCC CTG CAG GAG GAG GAG GAG CTG CAG CTG GCC CTG GCG CTG TCA CAG<br>Ala Leu Gln Glu Glu Glu Glu Leu Gln Leu Ala Leu Ala Leu Ser Gln<br>                      260                    265                  270 | 817 |
| TCA GAG GCG GAG GAG AAG GAG AGG CTG AGA CAG AAG TCC ACG TAC ACT<br>Ser Glu Ala Glu Glu Lys Glu Arg Leu Arg Gln Lys Ser Thr Tyr Thr<br>                      275                    280                  285 | 865 |
| TCT TAC CCC AAG GCG GAG CCC ATG CCC TCG GCC TCC TCA GCG CCC CCC<br>Ser Tyr Pro Lys Ala Glu Pro Met Pro Ser Ala Ser Ser Ala Pro Pro<br>                      290                    295                  300 | 913 |
| GCC AGC AGC CTG TAC TCT TCA CCT GTG AAC TCG TCG GCG CTT CTG GCT<br>Ala Ser Ser Leu Tyr Ser Ser Pro Val Asn Ser Ser Ala Leu Leu Ala<br>305                      310                    315 | 961 |
| GAG GAC ATC GAC CCT GAG CTC GCA CGG TAT CTC AAC CGG AAC TAC TGG<br>Glu Asp Ile Asp Pro Glu Leu Ala Arg Tyr Leu Asn Arg Asn Tyr Trp<br>320                      325                    330                  335 | 1009 |
| GAG AAG AAG CAG GAG GAG GCT CGC AAG AGC CCC ACG CCA TCT GCG CCC<br>Glu Lys Lys Gln Glu Glu Ala Arg Lys Ser Pro Thr Pro Ser Ala Pro<br>                      340                    345                  350 | 1057 |
| GTG CCC CTG ACG GAG CCG GCT GCA CAG CCT GGG GAA GGG CAC GCA GCC<br>Val Pro Leu Thr Glu Pro Ala Ala Gln Pro Gly Glu Gly His Ala Ala | 1105 |

-continued

```
              355                 360                 365
CCC ACC AAC GTG GTG GAG AAC CCC CTC CCG GAG ACA GAC TCT CAG CCC    1153
Pro Thr Asn Val Val Glu Asn Pro Leu Pro Glu Thr Asp Ser Gln Pro
            370                 375                 380

ATT CCT CCC TCT GGT GGC CCC TTT AGT GAG CCA CAG TTC CAC AAT GGC    1201
Ile Pro Pro Ser Gly Gly Pro Phe Ser Glu Pro Gln Phe His Asn Gly
        385                 390                 395

GAG TCT GAG GAG AGC CAC GAG CAG TTC CTG AAG GCG CTG CAG AAC GCC    1249
Glu Ser Glu Glu Ser His Glu Gln Phe Leu Lys Ala Leu Gln Asn Ala
400                 405                 410                 415

GTC ACC ACC TTC GTG AAC CGC ATG AAG AGT AAC CAC ATG CGG GGC CGC    1297
Val Thr Thr Phe Val Asn Arg Met Lys Ser Asn His Met Arg Gly Arg
                420                 425                 430

AGC ATC ACC AAT GAC TCG GCC GTG CTC TCA CTC TTC CAG TCC ATC AAC    1345
Ser Ile Thr Asn Asp Ser Ala Val Leu Ser Leu Phe Gln Ser Ile Asn
            435                 440                 445

GGC ATG CAC CCG CAG CTG CTG GAG CTG CTC AAC CAG CTG GAC GAG CGC    1393
Gly Met His Pro Gln Leu Leu Glu Leu Leu Asn Gln Leu Asp Glu Arg
        450                 455                 460

AGG CTG TAC TAT GAG GGG CTG CAG GAC AAG CTG GCA CAG ATC CGC GAT    1441
Arg Leu Tyr Tyr Glu Gly Leu Gln Asp Lys Leu Ala Gln Ile Arg Asp
465                 470                 475

GCC CGG GGG GCG CTG AGT GCC CTG CGC GAA GAG CAC CGG GAG AAG CTT    1489
Ala Arg Gly Ala Leu Ser Ala Leu Arg Glu Glu His Arg Glu Lys Leu
480                 485                 490                 495

CGC CGG GCA GCC GAG GAG GCA GAG CGC CAG CGC CAG ATC CAG CTG GCC    1537
Arg Arg Ala Ala Glu Glu Ala Glu Arg Gln Arg Gln Ile Gln Leu Ala
                500                 505                 510

CAG AAG CTG GAG ATA ATG CAT GGC GTG TAC ATG AGC CAG CCG GCC CCT    1585
Gln Lys Leu Glu Ile Met His Gly Val Tyr Met Ser Gln Pro Ala Pro
            515                 520                 525

GCC GCT GGC CCC TAC CCC AGC ATG CCC AGC ACT GCG GCT GAT CCC AGC    1633
Ala Ala Gly Pro Tyr Pro Ser Met Pro Ser Thr Ala Ala Asp Pro Ser
        530                 535                 540

ATG GTG AGT GCC TAC ATG TAC CCA GCA GGG GCC ACT GGG GCG CAG GCG    1681
Met Val Ser Ala Tyr Met Tyr Pro Ala Gly Ala Thr Gly Ala Gln Ala
545                 550                 555

GCC CCC CAG GCC CAG GCC GGA CCC ACC GCC AGC CCC GCT TAC TCA TCC    1729
Ala Pro Gln Ala Gln Ala Gly Pro Thr Ala Ser Pro Ala Tyr Ser Ser
560                 565                 570                 575

TAC CAG CCT ACT CCC ACA GCG GGC TAC CAG AAC GTG GCC TCC CAG GCC    1777
Tyr Gln Pro Thr Pro Thr Ala Gly Tyr Gln Asn Val Ala Ser Gln Ala
                580                 585                 590

CCA CAG AGC CTC CCG GCC ATC TCT CAG CCT CCG CAG TCC AGC ACC ATG    1825
Pro Gln Ser Leu Pro Ala Ile Ser Gln Pro Pro Gln Ser Ser Thr Met
            595                 600                 605

GGC TAC ATG GGG AGC CAG TCA GTC TCC ATG GGC TAC CAG CCT TAC AAC    1873
Gly Tyr Met Gly Ser Gln Ser Val Ser Met Gly Tyr Gln Pro Tyr Asn
        610                 615                 620

ATG CAG AAT CTC ATG ACC ACC CTC CCA AGC CAG GAT GCG TCT CTG CCA    1921
Met Gln Asn Leu Met Thr Thr Leu Pro Ser Gln Asp Ala Ser Leu Pro
625                 630                 635

CCC CAG CAG CCC TAC ATC GCG GGG CAG CAG CCC ATG TAC CAG CAG ATG    1969
Pro Gln Gln Pro Tyr Ile Ala Gly Gln Gln Pro Met Tyr Gln Gln Met
640                 645                 650                 655

GCA CCT TCT GGC GGT CCC CCC CAG CAG CAG CCC CCC GTG GCC CAG CAA    2017
Ala Pro Ser Gly Gly Pro Pro Gln Gln Gln Pro Pro Val Ala Gln Gln
                660                 665                 670

CCG CAG GCA CAG GGG CCG CCG GCA CAG GGC AGC GAG GCC CAG CTC ATT    2065
```

```
Pro Gln Ala Gln Gly Pro Pro Ala Gln Gly Ser Glu Ala Gln Leu Ile
              675                 680                 685

TCA TTC GAC TGACCCAGGC CATGCTCACG TCCGGAGTAA CACTACATAC              2114
Ser Phe Asp
        690

AGTTCACCTG AAACGCCTCG TCTCTAACTG CCGTCGTCCT GCCTCCCTGT CCTCTACTGC    2174

CGGTAGTGTC CCTTTCTCTG CGAGTGAGGG GGGGCTTTCA CCCCAAGCCC ACCTCCCTTG    2234

TCCTCAGCCT ACTGCAGTCC CTGAGTTAGT CTCTGCTTTC TTTCCCCAGG GCTGGGCCAT    2294

GGGGAGGGAA GGACTTTCTC CCAGGGGAAG CCCCCAGCCC TGTGGGTCAT GGTCTGTGAG    2354

AGGTGGCAGG AATGGGGACC CTCACCCCCC AAGCAGCCTG TGCCCTCTGG CCGCACTGTG    2414

AGCTGGCTGT GGTGTCTGGG TGTGGCCTGG GGCTCCCTCT GCAGGGGCCT CTCTCGGCAG    2474

CCACAGCCAA GGGTGGAGGC TTCAGGTCTC CAGCTTCTCT GCTTCTCAGC TGCCATCTCC    2534

AGTGCCCCAG AATGGTACAG CGATAATAAA ATGTATTTCA GAAAAAAAAA AAAAAAAAAA    2594

AAAAAAAAAA AAAAAAAAAA AAAAAAAAAA AAAAAAAAAA AAAAAAAAAA AAAAAAAAAA    2654

AAAAAAAAAA A                                                        2665

(2) INFORMATION FOR SEQ ID NO: 6:

(i) SEQUENCE CHARACTERISTICS:
        (A) LENGTH: 690 amino acids
        (B) TYPE: amino acid
        (D) TOPOLOGY: linear (ii) MOLECULE TYPE: protein (xi) SEQUENCE DESCRIPTION: SEQ ID NO: 6:

Met Gly Arg Gly Ser Gly Thr Phe Glu Arg Leu Leu Asp Lys Ala Thr
 1               5                  10                  15

Ser Gln Leu Leu Leu Glu Thr Asp Trp Glu Ser Ile Leu Gln Ile Cys
             20                  25                  30

Asp Leu Ile Arg Gln Gly Asp Thr Gln Ala Lys Tyr Ala Val Asn Ser
         35                  40                  45

Ile Lys Lys Lys Val Asn Asp Lys Asn Pro His Val Ala Leu Tyr Ala
 50                  55                  60

Leu Glu Val Met Glu Ser Val Val Lys Asn Cys Gly Gln Thr Val His
 65                  70                  75                  80

Asp Glu Val Ala Asn Lys Gln Thr Met Glu Glu Leu Lys Asp Leu Leu
                 85                  90                  95

Lys Arg Gln Val Glu Val Asn Val Arg Asn Lys Ile Leu Tyr Leu Ile
             100                 105                 110

Gln Ala Trp Ala His Ala Phe Arg Asn Glu Pro Lys Tyr Lys Val Val
         115                 120                 125

Gln Asp Thr Tyr Gln Ile Met Lys Val Glu Gly His Val Phe Pro Glu
130                 135                 140

Phe Lys Glu Ser Asp Ala Met Phe Ala Ala Glu Arg Ala Pro Asp Trp
145                 150                 155                 160

Val Asp Ala Glu Glu Cys His Arg Cys Arg Val Gln Phe Gly Val Met
                 165                 170                 175

Thr Arg Lys His His Cys Arg Ala Cys Gly Gln Ile Phe Cys Gly Lys
             180                 185                 190

Cys Ser Ser Lys Tyr Ser Thr Ile Pro Lys Phe Gly Ile Glu Lys Glu
         195                 200                 205

Val Arg Val Cys Glu Pro Cys Tyr Glu Gln Leu Asn Arg Lys Ala Glu
```

-continued

```
            210                 215                 220
Gly Lys Ala Thr Ser Thr Thr Glu Leu Pro Pro Asp Tyr Leu Thr Ser
225                 230                 235                 240

Pro Leu Ser Gln Gln Ser Gln Leu Pro Pro Lys Arg Asp Glu Thr Ala
                245                 250                 255

Leu Gln Glu Glu Glu Leu Gln Leu Ala Leu Ala Leu Ser Gln Ser
                260                 265                 270

Glu Ala Glu Glu Lys Glu Arg Leu Arg Gln Lys Ser Thr Tyr Thr Ser
                275                 280                 285

Tyr Pro Lys Ala Glu Pro Met Pro Ser Ala Ser Ser Ala Pro Pro Ala
        290                 295                 300

Ser Ser Leu Tyr Ser Ser Pro Val Asn Ser Ser Ala Leu Leu Ala Glu
305                 310                 315                 320

Asp Ile Asp Pro Glu Leu Ala Arg Tyr Leu Asn Arg Asn Tyr Trp Glu
                325                 330                 335

Lys Lys Gln Glu Glu Ala Arg Lys Ser Pro Thr Pro Ser Ala Pro Val
                340                 345                 350

Pro Leu Thr Glu Pro Ala Ala Gln Pro Gly Glu Gly His Ala Ala Pro
        355                 360                 365

Thr Asn Val Val Glu Asn Pro Leu Pro Glu Thr Asp Ser Gln Pro Ile
370                 375                 380

Pro Pro Ser Gly Gly Pro Phe Ser Glu Pro Gln Phe His Asn Gly Glu
385                 390                 395                 400

Ser Glu Glu Ser His Glu Gln Phe Leu Lys Ala Leu Gln Asn Ala Val
                405                 410                 415

Thr Thr Phe Val Asn Arg Met Lys Ser Asn His Met Arg Gly Arg Ser
                420                 425                 430

Ile Thr Asn Asp Ser Ala Val Leu Ser Leu Phe Gln Ser Ile Asn Gly
                435                 440                 445

Met His Pro Gln Leu Leu Glu Leu Leu Asn Gln Leu Asp Glu Arg Arg
        450                 455                 460

Leu Tyr Tyr Glu Gly Leu Gln Asp Lys Leu Ala Gln Ile Arg Asp Ala
465                 470                 475                 480

Arg Gly Ala Leu Ser Ala Leu Arg Glu Glu His Arg Glu Lys Leu Arg
                485                 490                 495

Arg Ala Ala Glu Glu Ala Glu Arg Gln Arg Gln Ile Gln Leu Ala Gln
                500                 505                 510

Lys Leu Glu Ile Met His Gly Val Tyr Met Ser Gln Pro Ala Pro Ala
        515                 520                 525

Ala Gly Pro Tyr Pro Ser Met Pro Ser Thr Ala Ala Asp Pro Ser Met
530                 535                 540

Val Ser Ala Tyr Met Tyr Pro Ala Gly Ala Thr Gly Ala Gln Ala Ala
545                 550                 555                 560

Pro Gln Ala Gln Ala Gly Pro Thr Ala Ser Pro Ala Tyr Ser Ser Tyr
                565                 570                 575

Gln Pro Thr Pro Thr Ala Gly Tyr Gln Asn Val Ala Ser Gln Ala Pro
        580                 585                 590

Gln Ser Leu Pro Ala Ile Ser Gln Pro Pro Gln Ser Ser Thr Met Gly
        595                 600                 605

Tyr Met Gly Ser Gln Ser Val Ser Met Gly Tyr Gln Pro Tyr Asn Met
        610                 615                 620

Gln Asn Leu Met Thr Thr Leu Pro Ser Gln Asp Ala Ser Leu Pro Pro
625                 630                 635                 640
```

```
Gln Gln Pro Tyr Ile Ala Gly Gln Gln Pro Met Tyr Gln Gln Met Ala
                645                 650                 655

Pro Ser Gly Gly Pro Pro Gln Gln Pro Pro Val Ala Gln Gln Pro
            660                 665                 670

Gln Ala Gln Gly Pro Pro Ala Gln Gly Ser Glu Ala Gln Leu Ile Ser
        675                 680                 685

Phe Asp
    690

(2) INFORMATION FOR SEQ ID NO: 7:

(i) SEQUENCE CHARACTERISTICS:
        (A) LENGTH: 158 base pairs
        (B) TYPE: nucleic acid
        (C) STRANDEDNESS: both
        (D) TOPOLOGY: both (ii) MOLECULE TYPE: cDNA (ix) FEATURE:
        (A) NAME/KEY: CDS
        (B) LOCATION: 2..157

(xi) SEQUENCE DESCRIPTION: SEQ ID NO: 7:

T GAG GAC TCG AGA GCC CTA AGG GAG CTC ATG GAG GGA GAG AGG GGT              46
  Glu Asp Ser Arg Ala Leu Arg Glu Leu Met Glu Gly Glu Arg Gly
  1               5                   10                  15

AAA CTG AGG CAA AGC CTA GAA GAG CTG CAG CGA CTC CAC AGT CAG GTG            94
Lys Leu Arg Gln Ser Leu Glu Glu Leu Gln Arg Leu His Ser Gln Val
            20                  25                  30

ACA CTG CTG AGT GTG GAG ATG ACT GCC CTA AAG AGG AGA GAG ACC GAC           142
Thr Leu Leu Ser Val Glu Met Thr Ala Leu Lys Arg Arg Glu Thr Asp
        35                  40                  45

TCA GAG TCA CTT CTG A                                                     158
Ser Glu Ser Leu Leu
        50

(2) INFORMATION FOR SEQ ID NO: 8:

(i) SEQUENCE CHARACTERISTICS:
        (A) LENGTH: 52 amino acids
        (B) TYPE: amino acid
        (D) TOPOLOGY: linear (ii) MOLECULE TYPE: protein (xi) SEQUENCE DESCRIPTION: SEQ ID NO: 8:

Glu Asp Ser Arg Ala Leu Arg Glu Leu Met Glu Gly Glu Arg Gly Lys
1               5                   10                  15

Leu Arg Gln Ser Leu Glu Glu Leu Gln Arg Leu His Ser Gln Val Thr
            20                  25                  30

Leu Leu Ser Val Glu Met Thr Ala Leu Lys Arg Arg Glu Thr Asp Ser
        35                  40                  45

Glu Ser Leu Leu
    50

(2) INFORMATION FOR SEQ ID NO: 9:

(i) SEQUENCE CHARACTERISTICS:
        (A) LENGTH: 666 base pairs
        (B) TYPE: nucleic acid
        (C) STRANDEDNESS: both
        (D) TOPOLOGY: both
```

-continued (ii) MOLECULE TYPE: cDNA (ix) FEATURE:
    (A) NAME/KEY: CDS
    (B) LOCATION: 2..175

(xi) SEQUENCE DESCRIPTION: SEQ ID NO: 9:

```
T GAC CTT ATT CTT AGA GCA AGT AGA TCT AAA TAT TTT TCA GCT GAG         46
  Asp Leu Ile Leu Arg Ala Ser Arg Ser Lys Tyr Phe Ser Ala Glu
   1               5                  10                  15

TTA TTA GGG AGT CAT TAT TCT GTG GTA CAA TGC TGC AAA AAG CAT CAT       94
Leu Leu Gly Ser His Tyr Ser Val Val Gln Cys Cys Lys Lys His His
             20                  25                  30

GTG GAA GAA TGG GAA CTA TGC TTA CTT TAT GAA GTG ATG TAT AAC ACA      142
Val Glu Glu Trp Glu Leu Cys Leu Leu Tyr Glu Val Met Tyr Asn Thr
             35                  40                  45

ATG AAA TCT GTT TTA CAA CTA AAA AAA AAA AAA NNNNNNNNNN NNNNNAATAT    195
Met Lys Ser Val Leu Gln Leu Lys Lys Lys Lys
             50                  55

GGACTTGGCA AGACTGAATC ATTTTACTGT GAAATATATA AACACAATAG AATGAGCCAA    255

CATGATGGTT TCTCTCCAGT AAGAGTTTTT CTTTTGGAAA TGAGGTTAAC CTAGCCCCAA    315

ATCTAGCAAT TGTGATAAAA TCCGATTTTA GAATTAGCCT CCCAGATTAA TCTGAATGAT    375

TGACTTATTT TTTCTTAGGC AAGTCAGTAA GCCACCCACT AGACAGCCAT ATCCAGCAAA    435

ATAAGAGAAG TTTCCAGATG CCAAATGATA AGCCACCATC AACCCAGCGG GGAGCCTTCT    495

GGTTGGTTTG GCTGTATGAG ATTCAGGAGG CCAGAATACC CAAAATTATT CACACGACGT    555

AACTTATTGG TACTGGCTAA GCAATACATG TATTTCCTAA AGGAGGAGAT GGTCTTTTGG    615

TTGATTTATG GACACACTTG TTTCATCTGA CTGTAAATAT ATTGCATGCT T             666
```

(2) INFORMATION FOR SEQ ID NO: 10:

(i) SEQUENCE CHARACTERISTICS:
        (A) LENGTH: 58 amino acids
        (B) TYPE: amino acid
        (D) TOPOLOGY: linear (ii) MOLECULE TYPE: protein (xi) SEQUENCE DESCRIPTION: SEQ ID NO: 10:

```
Asp Leu Ile Leu Arg Ala Ser Arg Ser Lys Tyr Phe Ser Ala Glu Leu
 1               5                  10                  15

Leu Gly Ser His Tyr Ser Val Val Gln Cys Cys Lys Lys His His Val
             20                  25                  30

Glu Glu Trp Glu Leu Cys Leu Leu Tyr Glu Val Met Tyr Asn Thr Met
             35                  40                  45

Lys Ser Val Leu Gln Leu Lys Lys Lys Lys
             50                  55
```

SCHWANNOMIN-BINDING PROTEINS

This application is a divisional of application Ser. No. 08/971,089, filed Nov. 14, 1997, now U.S. Pat. No. 6,376,174, which claims the benefit of priority of provisional application Ser. No. 60/030,987, filed Nov. 15, 1996, the contents of which is incorporated herein by reference.

FIELD OF THE INVENTION

The present invention relates to nucleic acids and proteins encoded thereby. Invention nucleic acids encode novel Schwannomin-Binding-Proteins. The invention also relates to methods for making and using such nucleic acids and proteins.

BACKGROUND OF THE INVENTION

The NF2 gene is the single most commonly mutated gene in benign tumors of the human nervous system. It is involved in the pathogenesis of virtually all schwannomas and many meningiomas (at least 50%) and ependymomas (Sainz et al., *Hum. Mol. Genet.* 3:885–891 (1994), Deprez et al., *Am. J. Hum. Genet.* 54:1022–1029 (1994), Rubio et al., *Cancer Res.* 54:45–47 (1994), Ruttledge et al, *Nature Genet.* 6:180–184 (1994), and Slavo et al., *Cancer* 64:243–247 (1995)). In addition to tumors, NF2 germline mutations also give rise to cataracts and retinal abnormalities such as hamartomas (Mautner et al., *Neurosurgery* 38:880–886 (1996)). The NF2 gene product is schwannomin (or merlin). Schwannomin is structurally similar to the ezrin-radixin-moesin (ERM) family of membrane-organizing proteins that link the plasma membrane and cytoskeleton (Rouleau et al., *Nature* 363:515–521 (1993) and Trofatter et al., *Cell* 72:791–800 (1993)). Schwannomin functions as a tumor suppressor, and as such is thought to have a role in a signal transduction pathway (Sainz et al., (1994), Huynh and Pulst, *Oncogene* 13:73–84 (1996), Tikoo et al., *J. Biol. Chem.* 269:23387–23390 (1994), and Twist et al., *Hum. Mol. Genet.* 3:147–151 (1994)). But other than its role in cell morphogenesis and adhesion (Huynh and Pulst (1996), supra), there is little additional knowledge of schwannomin function.

Therefore, there continues to be a need in the art for the discovery of additional proteins that interact with schwannomin, such as proteins that bind schwannomin in vivo, and especially a need for information serving to specifically identify and characterize such proteins in terms of their amino acid sequence. Moreover, to the extent that such molecules might form the basis for the development of therapeutic and diagnostic agents, it is essential that the DNA encoding them be elucidated. The present invention satisfies this need and provides related advantages as well.

BRIEF DESCRIPTION OF THE INVENTION

In accordance with the present invention, there are provided novel isolated nucleic acids encoding Schwannomin-Binding-Proteins (SBPs). Further provided are vectors containing invention nucleic acids, probes that hybridize thereto, host cells transformed therewith, antisense-nucleic acids thereto and related compositions. The nucleic acid molecules described herein can be incorporated into a variety of expression systems known to those of skill in the art. In addition, the nucleic acid molecules of the present invention are useful as probes for assaying for the presence and/or amount of a SBP gene or mRNA transcript in a given sample. The nucleic acid molecules described herein, and oligonucleotide fragments thereof, are also useful as primers and/or templates in a PCR reaction for amplifying genes encoding SBPs.

In accordance with the present invention, there are also provided isolated mammalian SBPs. These proteins, or fragments thereof, are useful in bioassays, as immunogens for producing anti-SBP antibodies, or in therapeutic compositions containing such proteins and/or antibodies. Also provided are transgenic non-human mammals that express the invention protein.

Antibodies that are immunoreactive with invention SBPs are also provided. These antibodies are useful in diagnostic assays to determine levels of SBPs present in a given sample, e.g., tissue samples, Western blots, and the like. The antibodies can also be used to purify SBPs from crude cell extracts and the like. Moreover, these antibodies are considered therapeutically useful to counteract or supplement the biological effect of SBPs in vivo.

Methods and diagnostic systems for determining the levels of SBP protein in various tissue samples are also provided. These diagnostic methods can be used for monitoring the level of therapeutically administered SBP or fragments thereof to facilitate the maintenance of therapeutically effective amounts. These diagnostic methods can also be used to diagnose physiological disorders that result from abnormal levels of SBP.

BRIEF DESCRIPTION OF THE FIGURES

FIG. 1 shows the interaction between βII-spectrin and schwannomin.

Figures 1A, 1B:
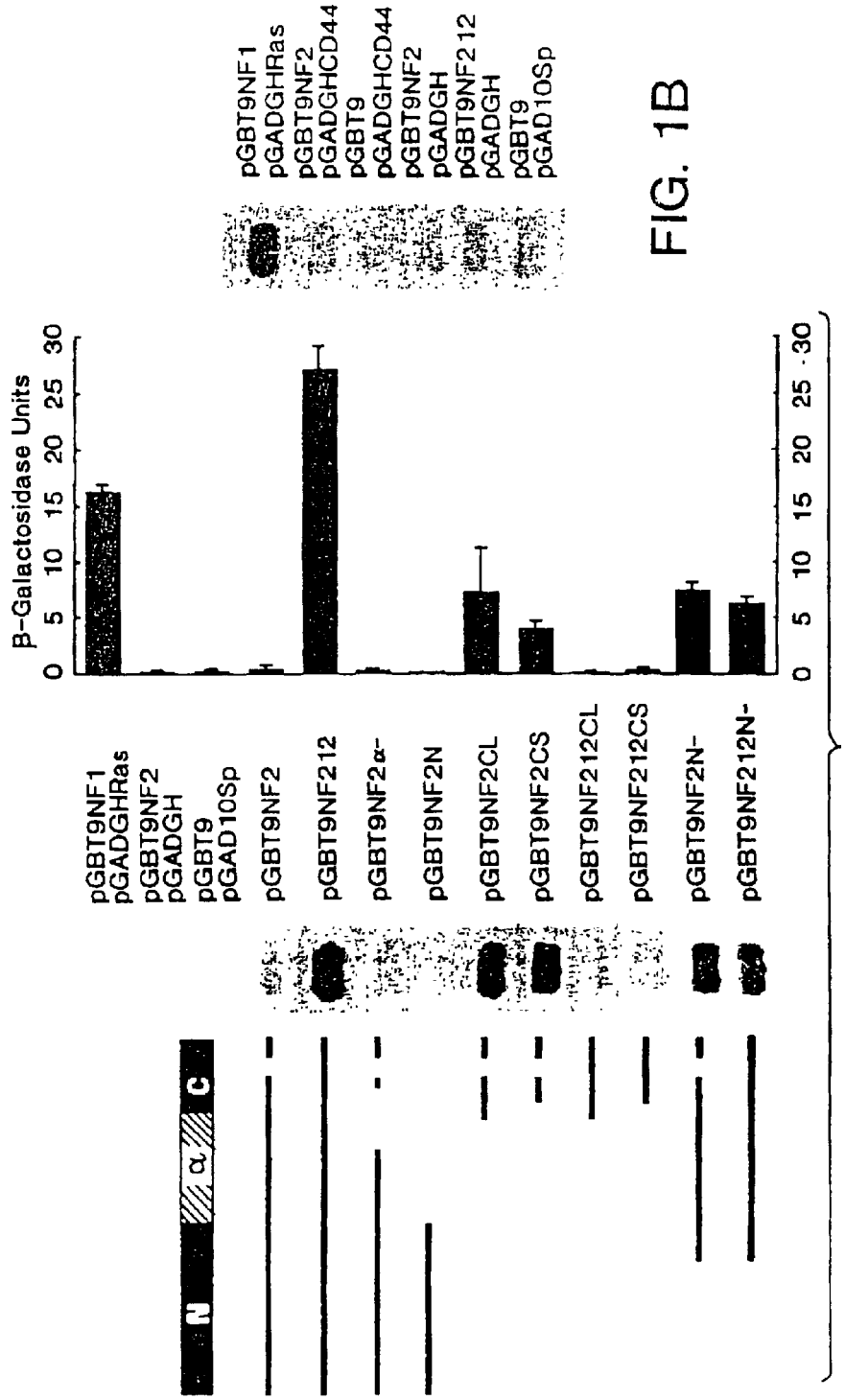
FIG. 1(A) Left: Cartoon of the NF2 gene with the three major domains drawn and regions cloned in pGBT9 indicated. The gap in the C-terminal domain of some constructs represents the absence or presence of exon 16, the difference between schwannomin isoforms 1 and 2; respectively. Plasmids encoding schwannomin have the following constructions: pGPT9NF2, residues 1–595; pGBT9NF212, residues 1–590; pGBT9NF2α-, Δ400–547; pGBT9NF2N, Δ306+; pGBT9NF2CL and pGBT9NF212CI, Δ1–468; pGPT9NF2CS and pGBT9NF212CS, Δ10518, pGBT9NF2C and pGBT9NF2I2C, Δ1–255. Center: β-galactosidase filter assays of double transformants of indicated pGBT9 constructs of the NF2 gene and pGAD10Sp. Blue colony color indicates the presence of β-galactosidase and a positive test of interaction between encoded proteins. Double-transformant pGBT9NF212CL and pGAD10Sp is weakly positive for β-galactosidase in the filter assay; the trace blue color is not visible in the photo. Right: Histogram illustrating results of semiquantitative liquid assays for β-galactosidase activity (Poullet and Tamanio, *Methods in Enzymol.* 255:488–497 (1995)). Three controls are included: pGBT9NF1 and pGADGHRas, negative pGBT9NF2 and pGADGH, negative pGBT9 and pGAD105p. β-Galactosidase units=1000× [$OD_{420}$/($OD_{600}$×times×culture volume)] Bars show mean and standard deviation of three replicate clones from one transformation. Except for pGBT9NF2C and pGBT9NF212C, liquid assays for each construct were conducted at the same time, and for all constructs, the same clones were used in filter assays, and results were reproducible.
FIG. 1(B) Control β-galactosidase filter assays of indicated double transformants showing high activity for a known positive interaction between NF1 and Ras (Poullet and Tamanio, (1995)), no detectable interaction between GAL4-NF2 and an unrelated protein, CD44 (conserved cytoplasmic domain, last 70 residues), and no detectable interaction between other negative controls.

Single bands of GSTNF2 and GSTNF212 proteins eluted from MBPSp-saturated amylose resin were detected using Ab5990, while bands that were not recognized by Ab5990 when GSTNF2 or GSTNF212 were incubated with amylose resin saturated with MBP with no fusion protein. The relative band intensities are consistent with differential binding strengths demonstrated in filter and liquid assays for β-galactosidase. Sizes are in kDa.

DETAILED DESCRIPTION OF THE INVENTION

In accordance with the present invention, there are provided isolated nucleic acids, which encode novel mammalian Schwannomin-Binding-Proteins (SBPs), and fragments thereof. As used herein, invention SBPs are those that have the ability to bind, preferably in vivo, to at least one isoform of a schwannomin protein encoded by an NF2 gene. The phrase "SBP" refers to substantially pure native SBP, or recombinantly produced proteins, including naturally occurring allelic variants thereof encoded by mRNA generated by alternative splicing of a primary transcript, and further including fragments thereof which retain at least one native biological activity, such as immunogenicity, the ability to bind to schwannomin, or the ability to bind to ribosomal DNA, ribosomal RNA, or ribosomal proteins. In another embodiment, SBPs referred to herein, are those polypeptides specifically recognized by an antibody that also specifically recognizes a SBP (preferably human) including an amino acid sequence set forth in SEQ ID NOs:2, 4, 6, 8 and 10. Invention isolated SBPs are free of cellular components and/or contaminants normally associated with a native in vivo environment.

The nucleic acid molecules described herein are useful for producing invention proteins, when such nucleic acids are incorporated into a variety of protein expression systems known to those of skill in the art. In addition, such nucleic acid molecules or fragments thereof can be labeled with a readily detectable substituent and used as hybridization probes for assaying for the presence and/or amount of an invention SBP gene or mRNA transcript in a given sample. The nucleic acid molecules described herein, and fragments thereof, are also useful as primers and/or templates in a PCR reaction for amplifying genes encoding invention proteins described herein.

The term "nucleic acid" (also referred to as polynucleotides) encompasses ribonucleic acid (RNA) or deoxyribonucleic acid (DNA), probes, oligonucleotides, and primers. DNA can be either complementary DNA (cDNA) or genomic DNA, e.g. a gene encoding a SBP. One means of isolating a nucleic acid encoding an SBP polypeptide is to probe a mammalian genomic library with a natural or artificially designed DNA probe using methods well known in the art. DNA probes derived from the SBP gene are particularly useful for this purpose. DNA and cDNA molecules that encode SBP polypeptides can be used to obtain complementary genomic DNA, cDNA or RNA from mammalian (e.g., human, mouse, rat, rabbit, pig, and the like), or other animal sources, or to isolate related cDNA or genomic clones by the screening of cDNA or genomic libraries, by methods described in more detail below. Examples of nucleic acids are RNA, cDNA, or isolated genomic DNA encoding an SBP polypeptide. Such nucleic acids may include, but are not limited to, nucleic acids comprising substantially the same nucleotide sequence as set forth in SEQ ID Nos:1, 3, 5, 7, and 9.

Use of the terms "isolated" and/or "purified" in the present specification and claims as a modifier of DNA, RNA, polypeptides or proteins means that the DNA, RNA, polypeptides or proteins so designated have been produced in such form by the hand of man, and thus are separated from their native in vivo cellular environment, and are substantially free of any other species of nucleic acid or protein. As a result of this human intervention, the recombinant DNAs, RNAs, polypeptides and proteins of the invention are useful in ways described herein that the DNAs, RNAs, polypeptides or proteins as they naturally occur are not.

As used herein, "mammalian" refers to the variety of species from which an invention SBP is derived, e.g., human, rat, mouse, rabbit, monkey, baboon, bovine, porcine, ovine, canine, feline, and the like. A preferred SBP herein, is human SBP.

In one embodiment of the present invention, cDNAs encoding the invention SBPs disclosed herein comprise substantially the same nucleotide sequence as set forth in any of SEQ ID NOs:1, 3, 5, 7 and 9. Preferred cDNA molecules encoding the invention proteins comprise the same nucleotide sequence as nucleotides 1–190 set forth in SEQ ID No:1; nucleotides 45–2783 set forth in SEQ ID NO:3; nucleotides 5–2074 set forth in SEQ ID NO:5; SEQ ID NO:7; or nucleotides 1–175 set forth in SEQ ID NO: 9.

As employed herein, the term "substantially the same nucleotide sequence" refers to DNA having sufficient identity to the reference polynucleotide, such that it will hybridize to the reference nucleotide under moderately stringent hybridization conditions. In one embodiment, DNA having substantially the same nucleotide sequence as the reference nucleotide sequence encodes substantially the same amino acid sequence as that set forth in any of SEQ ID Nos:2, 4, 6, 8, or 10. In another embodiment, DNA having "substantially the same nucleotide sequence" as the reference nucleotide sequence has at least 60% identity with respect to the reference nucleotide sequence. DNA having at least 70%, more preferably at least 90%, yet more preferably at least 95%, identity to the reference nucleotide sequence is preferred.

This invention also encompasses nucleic acids which differ from the nucleic acids shown in SEQ ID NOs:1, 3, 5, 7 and 9, but which have the same phenotype. Phenotypically similar nucleic acids are also referred to as "functionally equivalent nucleic acids". As used herein, the phrase "functionally equivalent nucleic acids" encompasses nucleic acids characterized by slight and non-consequential sequence variations that will function in substantially the same manner to produce the same protein product(s) as the nucleic acids disclosed herein. In particular, functionally equivalent nucleic acids encode polypeptides that are the same as those encoded by the nucleic acids disclosed herein or that have conservative amino acid variations. For example, conservative variations include substitution of a non-polar residue with another non-polar residue, or substitution of a charged residue with a similarly charged residue. These variations include those recognized by skilled artisans as those that do not substantially alter the tertiary structure of the protein.

Further provided are nucleic acids encoding SBP polypeptides that, by virtue of the degeneracy of the genetic code, do not necessarily hybridize to the invention nucleic acids under specified hybridization conditions. Preferred nucleic acids encoding the invention SBPs are comprised of nucleotides that encode substantially the same amino acid sequence as set forth in SEQ ID Nos:2, 4, 6, 8, or 10.

Thus, an exemplary nucleic acid encoding an invention SBP may be selected from:

(a) DNA encoding the amino acid sequence set forth in SEQ ID Nos:2, 4, 6, 8 or 10, (b) DNA that hybridizes to the DNA of (a) under moderately stringent conditions, wherein said DNA encodes biologically active SBP, or (c) DNA degenerate with respect to either (a) or (b) above, wherein said DNA encodes biologically active SBP.

Hybridization refers to the binding of complementary strands of nucleic acid (i.e., sense:antisense strands or probe:target-DNA) to each other through hydrogen bonds, similar to the bonds that naturally occur in chromosomal DNA. Stringency levels used to hybridize a given probe with target-DNA can be readily varied by those of skill in the art.

The phrase "stringent hybridization" is used herein to refer to conditions under which polynucleic acid hybrids are stable. As known to those of skill in the art, the stability of hybrids is reflected in the melting temperature ($T_m$) of the hybrids. In general, the stability of a hybrid is a function of sodium ion concentration and temperature. Typically, the hybridization reaction is performed under conditions of lower stringency, followed by washes of varying, but higher, stringency. Reference to hybridization stringency relates to such washing conditions.

As used herein, the phrase "moderately stringent hybridization" refers to conditions that permit target-DNA to bind a complementary nucleic acid that has about 60% identity, preferably about 75% identity, more preferably about 85% identity to the target DNA; with greater than about 90% identity to target-DNA being especially preferred. Preferably, moderately stringent conditions are conditions equivalent to hybridization in 50% formamide, 5× Denhart's solution, 5× SSPE, 0.2% SDS at 42° C., followed by washing in 0.2× SSPE, 0.2% SDS, at 65° C.

The phrase "high stringency hybridization" refers to conditions that permit hybridization of only those nucleic acid sequences that form stable hybrids in 0.018M NaCl at 65° C. (i.e., if a hybrid is not stable in 0.018M NaCl at 65° C., it will not be stable under high stringency conditions, as contemplated herein). High stringency conditions can be provided, for example, by hybridization in 50% formamide, 5× Denhart's solution, 5× SSPE, 0.2% SDS at 42° C., followed by washing in 0.1× SSPE, and 0.1% SDS at 65° C.

The phrase "low stringency hybridization" refers to conditions equivalent to hybridization in 10% formamide, 5× Denhart's solution, 6× SSPE, 0.2% SDS at 42° C., followed by washing in 1× SSPE, 0.2% SDS, at 50° C. Denhart's solution and SSPE (see, e.g., Sambrook et al., *Molecular Cloning. A Laboratory Manual*, Cold Spring Harbor Laboratory Press, 1989) are well known to those of skill in the art as are other suitable hybridization buffers.

As used herein, the term "degenerate" refers to codons that differ in at least one nucleotide from a reference nucleic acid, e.g., SEQ ID NOs:1, 3, 5, 7 and 9, but encode the same amino acids as the reference nucleic acid. For example, codons specified by the triplets "UCU", "UCC", "UCA", and "UCG" are degenerate with respect to each other since all four of these codons encode the amino acid serine.

Preferred nucleic acids encoding the invention polypeptide(s) hybridize under moderately stringent, preferably high stringency, conditions to substantially the entire sequence, or substantial portions (i.e., typically at least 15–30 nucleotides) of the nucleic acid sequence set forth in SEQ ID NOs:1, 3, 5, 7 and 9.

The invention nucleic acids can be produced by a variety of methods well-known in the art, e.g., the methods described herein, employing PCR amplification using oligonucleotide primers from various regions of SEQ ID NOs:1, 3, 5, 7 and 9, and the like.

In accordance with a further embodiment of the present invention, optionally labeled SBP-encoding cDNAs, or fragments thereof, can be employed to probe library(ies) (e.g., cDNA, genomic, and the like) for additional nucleic acid sequences encoding novel mammalian SBPs. Construction of suitable mammalian cDNA libraries is well-known in the art. Screening of such a cDNA library is initially carried out under low-stringency conditions, which comprise a temperature of less than about 42° C., a formamide concentration of less than about 50%, and a moderate to low salt concentration.

Presently preferred probe-based screening conditions comprise a temperature of about 37° C., a formamide concentration of about 20%, and a salt concentration of about 5× standard saline citrate (SSC; 20× SSC contains 3M sodium chloride, 0.3M sodium citrate, pH 7.0). Such conditions will allow the identification of sequences which have a substantial degree of similarity with the probe sequence, without requiring perfect homology. The phrase "substantial similarity" refers to sequences which share at least 50% homology. Preferably, hybridization conditions will be selected which allow the identification of sequences having at least 70% homology with the probe, while discriminating against sequences which have a lower degree of homology with the probe. As a result, nucleic acids having substantially the same nucleotide sequence as SEQ ID NOs:1, 3, 5, 7 and 9 are obtained.

As used herein, a nucleic acid "probe" is single-stranded DNA or RNA, or analogs thereof, that has a sequence of nucleotides that includes at least 14, at least 20, at least 50, at least 100, at least 200, at least 300, at least 400, or at least 500 contiguous bases that are the same as (or the complement of) any contiguous bases set forth in any of SEQ ID NOs:1, 3, 5, 7 and 9. Preferred regions from which to construct probes include 5' and/or 3' coding regions of SEQ ID NOs:1, 3, 5, 7 and 9. In addition, the entire cDNA encoding region of an invention SBP, or the entire sequence corresponding to SEQ ID NOs:1, 3, 5, 7 and 9, may be used as a probe. Probes may be labeled by methods well-known in the art, as described hereinafter, and used in various diagnostic kits.

As used herein, the terms "label" and "indicating means" in their various grammatical forms refer to single atoms and molecules that are either directly or indirectly involved in the production of a detectable signal. Any label or indicating means can be linked to invention nucleic acid probes, expressed proteins, polypeptide fragments, or antibody molecules. These atoms or molecules can be used alone or in conjunction with additional reagents. Such labels are themselves well-known in clinical diagnostic chemistry.

The labeling means can be a fluorescent labeling agent that chemically binds to antibodies or antigens without denaturation to form a fluorochrome (dye) that is a useful immunofluorescent tracer. A description of immunofluorescent analytic techniques is found in DeLuca, "Immunofluorescence Analysis", in *Antibody As a Tool*, Marchalonis et al., eds., John Wiley & Sons, Ltd., pp. 189–231 (1982), which is incorporated herein by reference.

In one embodiment, the indicating group is an enzyme, such as horseradish peroxidase (HRP), glucose oxidase, and the like. In another embodiment, radioactive elements are employed labeling agents. The linking of a label to a substrate, i.e., labeling of nucleic acid probes, antibodies, polypeptides, and proteins, is well known in the art. For instance, an invention antibody can be labeled by metabolic incorporation of radiolabeled amino acids provided in the culture medium. See, for example, Galfre et al., *Meth. Enzymol.*, 73:3–46 (1981). Conventional means of protein conjugation or coupling by activated functional groups are particularly applicable. See, for example, Aurameas et al., *Scand. J. Immunol.*, Vol. 8, Suppl. 7:7–23 (1978), Rodwell et al., *Biotech.*, 3:889–894 (1984), and U.S. Pat. No. 4,493,795.

In accordance with another embodiment of the present invention, there are provided isolated mammalian Schwannomin-Binding-Proteins (SBPs), and fragments thereof encoded by invention nucleic acid. The phrase "SBP" refers to substantially pure native SBP, or recombinantly produced proteins, including naturally occurring allelic variants thereof encoded by mRNA generated by alternative splicing of a primary transcript, and further including fragments thereof which retain at least one native biological activity, such as immunogenicity, the ability to bind to schwannomin, or the ability to bind to ribosomal DNA, ribosomal RNA, or ribosomal proteins. Invention SBPs are characterized by having the ability to bind to at least one isoform of a schwannomin protein encoded by an NF2 gene. In another embodiment, SBPs referred to herein, are those polypeptides specifically recognized by an antibody that also specifically recognizes a SBP (preferably human) including an amino acid sequence set forth in SEQ ID NOs:2, 4, 6, 8 and 10. Invention isolated SBPs are free of cellular components and/or contaminants normally associated with a native in vivo environment.

The invention proteins are further characterized by being ubiquitously expressed, including expression in adult brain. Splice variant cDNA transcripts encoding a SBP family of proteins are also contemplated by the present invention.

Presently preferred SBPs of the invention include amino acid sequences that comprise substantially the same as the protein sequence set forth in SEQ ID NOs:2, 4, 6, 8 and 10, as well as biologically active, modified forms thereof. As discussed above, each of the invention SBP proteins bind to the neurofibromatosis 2 (NF2) tumor suppressor protein schwannomin. The SBP set forth in SEQ ID NO:4 was identified in a screen of binding proteins using schwannomin isoform 1, while invention SBPs set forth in SEQ ID Nos:2, 6, 8 and 10 were identified in a screen with schwannomin isoform 2. In addition, the invention SBP protein corresponding to SEQ ID NO:4 has been found to have functional involvement in the initiation of translation and is contemplated herein as serving a role in the final steps of a signal transduction cascade affecting cell division and proliferation.

In addition, it has been found that the SBP protein set forth in SEQ ID NO:6 binds with high affinity to schwannomin isoform 2 while demonstrating very little, if any, binding affinity for schwannomin isoform 1; the SBP set forth in SEQ ID No:6 is referred to herein as an isoform-specific schwannomin binding protein. The invention SBP protein corresponding to SEQ ID NO:6 has been found to be multifunctional, with ATPase activity, and involvment in $Ca^{2+}$ secretion and $Zn^{2+}$ binding. The SBP corresponding to SEQ ID NO:6 is phosphorylated by growth factor and is involved in a pathway of signal transduction. The SBP protein (SEQ ID NO:6) contains a zinc finger domain which has a known function in binding DNA and RNA and is contemplated as being involved in the regulation of transcription and thus cell proliferation. The invention SBP protein fragment corresponding to SEQ ID NO:10 has been found to encode polylysine which is a feature of a variety of transcriptional regulators.

Those of skill in the art will recognize that numerous residues of the above-described sequences can be substituted with other, chemically, sterically and/or electronically similar residues without substantially altering the biological activity of the resulting receptor species. In addition, larger polypeptide sequences containing substantially the same sequence as amino acids set forth in SEQ ID NOs:2, 4, 6, 8 and 10 therein (e.g., splice variants) are contemplated.

As employed herein, the term "substantially the same amino acid sequence" refers to amino acid sequences having at least about 70% identity with respect to the reference amino acid sequence, and retaining comparable functional and biological activity characteristic of the protein defined by the reference amino acid sequence. Preferably, proteins having "substantially the same amino acid sequence" will have at least about 80%, more preferably 90% amino acid identity with respect to the reference amino acid sequence; with greater than about 95% amino acid sequence identity being especially preferred. It is recognized, however, that polypeptides (or nucleic acids referred to hereinbefore) containing less than the described levels of sequence identity arising as splice variants or that are modified by conservative amino acid substitutions, or by substitution of degenerate codons are also encompassed within the scope of the present invention.

The term "biologically active" or "functional", when used herein as a modifier of invention SBP(s), or polypeptide fragment thereof, refers to a polypeptide that exhibits functional characteristics similar to SBP. For example, one biological activity of SBP is the ability to bind, preferably in vivo, to at least one isoform of a schwannomin protein encoded by an NF2 gene. Such schwannomin binding activity can be assayed, for example, using the methods described in Examples I or III herein. Another biological activity of SBP is the ability to act as an immunogen for the production of polyclonal and monoclonal antibodies that bind specifically to an invention SBP. Thus, an invention nucleic acid encoding SBP will encode a polypeptide specifically recognized by an antibody that also specifically recognizes the SBP protein (preferably human) including the amino acid set forth in SEQ ID NOs:2, 4, 6, 8 and 10. Such immunologic activity may be assayed by any method known to those of skill in the art. For example, a test-polypeptide encoded by a SBP cDNA can be used to produce antibodies, which are then assayed for their ability to bind to an invention SBP protein including the sequence set forth in SEQ ID Nos:2, 4, 6, 8 or 10. If the antibody binds to the test-polypeptide and the protein including the sequence encoded by SEQ ID NOs:2, 4, 6, 8 or 10 with substantially the same affinity, then the polypeptide possesses the requisite immunologic biological activity.

The invention SBPs can be isolated by a variety of methods well-known in the art, e.g., recombinant expression systems described herein, precipitation, gel filtration, ion-exchange, reverse-phase and affinity chromatography, and the like. Other well-known methods are described in Deutscher et al., *Guide to Protein Purification: Methods in Enzymology* Vol. 182, (Academic Press, (1990)), which is incorporated herein by reference. Alternatively, the isolated polypeptides of the present invention can be obtained using well-known recombinant methods as described, for example, in Sambrook et al., supra., 1989).

An example of the means for preparing the invention polypeptide(s) is to express nucleic acids encoding the SBP in a suitable host cell, such as a bacterial cell, a yeast cell, an amphibian cell (i.e., oocyte), or a mammalian cell, using methods well known in the art, and recovering the expressed polypeptide, again using well-known methods. Invention polypeptides can be isolated directly from cells that have been transformed with expression vectors as described below herein. The invention polypeptide, biologically functional fragments, and functional equivalents thereof can also be produced by chemical synthesis. For example, synthetic polypeptides can be produced using Applied Biosystems, Inc. Model 430A or 431A automatic peptide synthesizer (Foster City, Calif.) employing the chemistry provided by the manufacturer.

Also encompassed by the term SBP are functional fragments or polypeptide analogs thereof. The term "functional fragment" refers to a peptide fragment that is a portion of a full length SBP protein, provided that the portion has a biological activity, as defined above, that is characteristic of the corresponding full length protein. For example, a functional fragment of an invention SBP protein, such as a schwannomin-binding domain can have an activity such as the ability, for example, to bind schwannomin or to modulate the level of cell proliferation, such as in tumors, after binding to schwannomin. In addition, the characteristic of a functional fragment of invention SBP proteins to elicit an immune response is useful for obtaining an anti-SBP antibodies. Thus, the invention also provides functional fragments of invention SBP proteins, which can be identified using the binding and routine methods, such as bioassays described herein.

The term "polypeptide analog" includes any polypeptide having an amino acid residue sequence substantially the same as a sequence specifically shown herein in which one or more residues have been conservatively substituted with a functionally similar residue and which displays the ability to functionally mimic an SBP as described herein. Examples of conservative substitutions include the substitution of one non-polar (hydrophobic) residue such as isoleucine, valine, leucine or methionine for another, the substitution of one polar (hydrophilic) residue for another such as between arginine and lysine, between glutamine and asparagine, between glycine and serine, the substitution of one basic residue such as lysine, arginine or histidine for another, or the substitution of one acidic residue, such as aspartic acid or glutamic acid for another.

The amino acid length of functional fragments or polypeptide anlogs of the present invention can range from about 5 amino acids up to the full-length protein sequence of an invention SBP. In certain embodiments, the amino acid lengths include, for example, at least about 10 amino acids, at least about 20, at least about 30, at least about 40, at least about 50, at least about 75, at least about 100, at least about 150, at least about 200, at least about 250 or more amino acids in length up to the full-length SBP protein sequence.

As used herein the phrase "conservative substitution" also includes the use of a chemically derivatized residue in place of a non-derivatized residue, provided that such polypeptide displays the required binding activity. The phrase "chemical derivative" refers to a subject polypeptide having one or more residues chemically derivatized by reaction of a functional side group. Such derivatized molecules include, for example, those molecules in which free amino groups have been derivatized to form amine hydrochlorides, p-toluene sulfonyl groups, carbobenzoxy groups, t-butyloxycarbonyl groups, chloroacetyl groups or formyl groups. Free carboxyl groups may be derivatized to form salts, methyl and ethyl esters or other types of esters or hydrazides. Free hydroxyl groups may be derivatized to form O-acyl or O-alkyl derivatives. The imidazole nitrogen of histidine may be derivatized to form N-im-benzylhistidine. Also included as chemical derivatives are those peptides which contain one or more naturally occurring amino acid derivatives of the twenty standard amino acids. For examples: 4-hydroxyproline may be substituted for proline; 5-hydroxylysine may be substi-tuted for lysine; 3-methylhistidine may be substituted for histidine; homoserine may be substituted for serine; and ornithine may be substituted for lysine. Polypeptides of the present invention also include any polypeptide having one or more additions and/or deletions of residues, relative to the sequence of a polypeptide whose sequence is shown herein, so long as the required activity is maintained.

The present invention also provides compositions containing an acceptable carrier and any of an isolated, purified SBP mature protein or functional polypeptide fragments thereof, alone or in combination with each other. These polypeptides or proteins can be recombinantly derived, chemically synthesized or purified from native sources. As used herein, the term "acceptable carrier" encompasses any of the standard pharmaceutical carriers, such as phosphate buffered saline solution, water and emulsions such as an oil/water or water/oil emulsion, and various types of wetting agents.

The SBP compositions described herein can be used, for example, in methods for modulating the activity of schwannomin proteins, or other oncogenic proteins, such as retinoblastomo, p53, ras, and the like. Thus, in accordance with another embodiment of the invention, there are provided methods for modulating the activity of an oncogenic protein, preferably schwannomin protein, comprising contacting the oncogenic protein with a substantially pure SBP, or an oncogenic proteins-binding fragment thereof. As used herein the phrase "modulating the activity" or grammatical variations thereof, refers to either inhibition of oncogenic protein activity (as with an antagonist) or the activation of schwannomin activity (as with an agonist). For example, schwannomin activities contemplated herein for modulation include, for example, tumor suppressing activity, cell proliferation activity, ribosomal DNA-binding activity, and the like.

Also provided are antisense-nucleic acids having a sequence capable of binding specifically with full-length or any portion of an mRNA that encodes SBP polypeptides so as to prevent translation of the mRNA. The antisense-nucleic acid may have a sequence capable of binding specifically with any portion of the sequence of the cDNA encoding SBP polypeptides. As used herein, the phrase "binding specifically" encompasses the ability of a nucleic acid sequence to recognize a complementary nucleic acid sequence and to form double-helical segments therewith via the formation of hydrogen bonds between the complementary base pairs. An example of an antisense-nucleic acid is an antisense-nucleic acid comprising chemical analogs of nucleotides.

Compositions comprising an amount of the antisense-nucleic acid, described above, effective to reduce expression of SBP polypeptides by passing through a cell membrane and binding specifically with mRNA encoding SBP polypeptides so as to prevent translation and an acceptable hydrophobic carrier capable of passing through a cell membrane are also provided herein. Suitable hydrophobic carriers are described, for example, in U.S. Pat. Nos. 5,334,761; 4,889,953; 4,897,355, and the like. The acceptable hydrophobic carrier capable of passing through cell membranes may also comprise a structure which binds to a receptor specific for a selected cell type and is thereby taken up by cells of the selected cell type. The structure may be part of a protein known to bind to a cell-type specific receptor.

Antisense-nucleic acid compositions are useful to inhibit translation of mRNA encoding invention polypeptides. Synthetic oligonucleotides, or other antisense chemical structures are designed to bind to mRNA encoding SBP polypeptides and inhibit translation of mRNA and are useful as compositions to inhibit expression of SBP associated genes in a tissue sample or in a subject.

In accordance with another embodiment of the invention, kits for detecting mutations, duplications, deletions, rearrangements and aneuploidies in SBP genes comprising at least one invention probe or antisense nucleotide.

The present invention provides means to modulate levels of expression of SBP polypeptides by employing synthetic antisense-nucleic acid compositions (hereinafter SANC) which inhibit translation of mRNA encoding these polypeptides. Synthetic oligonucleotides, or other antisense-nucleic acid chemical structures designed to recognize and selectively bind to mRNA, are constructed to be complementary to full-length or portions of an SBP coding strand, including nucleotide sequences set forth in SEQ ID NOs:1, 3, 5, 7 and 9. The SANC is designed to be stable in the blood stream for administration to a subject by injection, or in laboratory cell culture conditions. The SANC is designed to be capable of passing through the cell membrane in order to enter the cytoplasm of the cell by virtue of physical and chemical properties of the SANC which render it capable of passing through cell membranes, for example, by designing small, hydrophobic SANC chemical structures, or by virtue of specific transport systems in the cell which recognize and transport the SANC into the cell. In addition, the SANC can be designed for administration only to certain selected cell populations by targeting the SANC to be recognized by specific cellular uptake mechanisms which bind and take up the SANC only within select cell populations. In a particular embodiment the SANC is an antisense oligonucleotide.

For example, the SANC may be designed to bind to a receptor found only in a certain cell type, as discussed supra. The SANC is also designed to recognize and selectively bind to target mRNA sequence, which may correspond to a sequence contained within the sequences shown in SEQ ID NOs:1, 3, 5, 7 and 9. The SANC is designed to inactivate target mRNA sequence by either binding thereto and inducing degradation of the mRNA by, for example, RNase I digestion, or inhibiting translation of mRNA target sequence by interfering with the binding of translation-regulating factors or ribosomes, or inclusion of other chemical structures, such as ribozyme sequences or reactive chemical groups which either degrade or chemically modify the target mRNA. SANCs have been shown to be capable of such properties when directed against mRNA targets (see Cohen et al., *TIPS*, 10:435 (1989) and Weintraub, *Sci. American*, January (1990), pp.40; both incorporated herein by reference).

In accordance with yet another embodiment of the present invention, there is provided a method for the recombinant production of invention SBPs by expressing the above-described nucleic acid sequences in suitable host cells. Recombinant DNA expression systems that are suitable to produce SBPs described herein are well-known in the art. For example, the above-described nucleotide sequences can be incorporated into vectors for further manipulation. As used herein, vector (or plasmid) refers to discrete elements that are used to introduce heterologous DNA into cells for either expression or replication thereof.

Suitable expression vectors are well-known in the art, and include vectors capable of expressing DNA operatively linked to a regulatory sequence, such as a promoter region that is capable of regulating expression of such DNA. Thus, an expression vector refers to a recombinant DNA or RNA construct, such as a plasmid, a phage, recombinant virus or other vector that, upon introduction into an appropriate host cell, results in expression of the inserted DNA. Appropriate expression vectors are well known to those of skill in the art and include those that are replicable in eukaryotic cells and/or prokaryotic cells and those that remain episomal or those which integrate into the host cell genome.

As used herein, a promoter region refers to a segment of DNA that controls transcription of DNA to which it is operatively linked. The promoter region includes specific sequences that are sufficient for RNA polymerase recognition, binding and transcription initiation. In addition, the promoter region includes sequences that modulate this recognition, binding and transcription initiation activity of RNA polymerase. These sequences may be cis acting or may be responsive to trans acting factors. Promoters, depending upon the nature of the regulation, may be constitutive or regulated. Exemplary promoters contemplated for use in the practice of the present invention include the SV40 early promoter, the cytomegalovirus (CMV) promoter, the mouse mammary tumor virus (MMTV) steroid-inducible promoter, Moloney murine leukemia virus (MMLV) promoter, and the like.

As used herein, the term "operatively linked" refers to the functional relationship of DNA with regulatory and effector nucleotide sequences, such as promoters, enhancers, transcriptional and translational stop sites, and other signal sequences. For example, operative linkage of DNA to a promoter refers to the physical and functional relationship between the DNA and the promoter such that the transcription of such DNA is initiated from the promoter by an RNA polymerase that specifically recognizes, binds to and transcribes the DNA.

As used herein, expression refers to the process by which polynucleic acids are transcribed into mRNA and translated into peptides, polypeptides, or proteins. If the polynucleic acid is derived from genomic DNA, expression may, if an appropriate eukaryotic host cell or organism is selected, include splicing of the mRNA.

Prokaryotic transformation vectors are well-known in the art and include pBlueskript and phage Lambda ZAP vectors (Stratagene, La Jolla, Calif.), and the like. Other suitable vectors and promoters are disclosed in detail in U.S. Pat. No. 4,798,885, issued Jan. 17, 1989, the disclosure of which is incorporated herein by reference in its entirety.

Other suitable vectors for transformation of *E. coli* cells include the pET expression vectors (Novagen, see U.S. Pat. No. 4,952,496), e.g., pET11a, which contains the T7 promoter, T7 terminator, the inducible *E. coli* lac operator, and the lac repressor gene; and pET 12a–c, which contain the T7 promoter, T7 terminator, and the *E. coli* ompT secretion signal. Another suitable vector is the pIN-IIIompA2 (see Duffaud et al., *Meth. in Enzymology*, 153:492–507, 1987), which contains the lpp promoter, the lacUV5 promoter operator, the ompA secretion signal, and the lac repressor gene.

Exemplary, eukaryotic transformation vectors, include the cloned bovine papilloma virus genome, the cloned genomes of the murine retroviruses, and eukaryotic cassettes, such as the pSV-2 gpt system [described by Mulligan and Berg, *Nature* Vol. 277:108–114 (1979)] the Okayama-Berg cloning system [*Mol. Cell Biol.* Vol. 2:161–170 (1982)], and the expression cloning vector described by Genetics Institute [*Science* Vol. 228:810–815 (1985)], are available which provide substantial assurance of at least some expression of the protein of interest in the transformed eukaryotic cell line.

Particularly preferred base vectors which contain regulatory elements that can be linked to the invention SBP-encoding DNAs for transfection of mammalian cells are cytomegalovirus (CMV) promoter-based vectors such as pcDNA1 (Invitrogen, San Diego, Calif.), MMTV promoter-based vectors such as pMAMNeo (Clontech, Palo Alto, Calif.) and pMSG (Pharmacia, Piscataway, N.J.), and SV40 promoter-based vectors such as pSVβ (Clontech, Palo Alto, Calif.).

In accordance with another embodiment of the present invention, there are provided "recombinant cells" containing the nucleic acid molecules (i.e., DNA or mRNA) of the present invention. Methods of transforming suitable host cells, preferably bacterial cells, and more preferably *E. coli* cells, as well as methods applicable for culturing said cells containing a gene encoding a heterologous protein, are generally known in the art. See, for example, Sambrook et al., *Molecular Cloning*: A Laboratory Manual (2 ed.), Cold Spring Harbor Laboratory Press, Cold Spring Harbor, N.Y., USA (1989).

Exemplary methods of transformation include, e.g., transformation employing plasmids, viral, or bacterial phage vectors, transfection, electroporation, lipofection, and the like. The heterologous DNA can optionally include sequences which allow for its extrachromosomal maintenance, or said heterologous DNA can be caused to integrate into the genome of the host (as an alternative means to ensure stable maintenance in the host).

Host organisms contemplated for use in he practice of the present invention include those organisms in which recombinant production of heterologous proteins has been carried out. Examples of such host organisms include bacteria (e.g., *E. coli*), yeast (e.g., *Saccharomyces cerevisiae, Candida tropicalis, Hansenula polymorpha* and *P. pastoris*; see, e.g., U.S. Pat. Nos. 4,882,279, 4,837,148, 4,929,555 and 4,855,231), mammalian cells (e.g., HEK293, CHO and Ltk⁻ cells), insect cells, and the like. Presently preferred host organisms are bacteria. The most preferred bacteria is *E. coli*.

In one embodiment, nucleic acids encoding the invention SBPs can be delivered into mammalian cells, either in vivo or in vitro using suitable viral vectors well-known in the art. Suitable retroviral vectors, designed specifically for "gene therapy" methods, are described, for example, in WIPO publications WO 9205266 and WO 9214829, which provide a description of methods for efficiently introducing nucleic acids into human cells. In addition, where it is desirable to limit or reduce the in vivo expression of the invention SBP, the introduction of the antisense strand of the invention nucleic acid is contemplated.

Viral based systems provide the advantage of being able to introduce relatively high levels of the heterologous nucleic acid into a variety of cells. Suitable viral vectors for introducing invention nucleic acid encoding an SBP protein into mammalian cells (e.g., vascular tissue segments) are well known in the art. These viral vectors include, for example, Herpes simplex virus vectors (e.g., Geller et al., *Science*, 241:1667–1669 (1988)), Vaccinia virus vectors (e.g., Piccini et al., *Meth. in Enzymology*, 153:545–563 (1987); Cytomegalovirus vectors (Mocarski et al., in *Viral Vectors*, Y. Gluzman and S. H. Hughes, Eds., Cold Spring Harbor Laboratory, Cold Spring Harbor, N.Y., 1988, pp. 78–84), Moloney murine leukemia virus vectors (Danos et al., *PNAS. USA*, 85:6469 (1980)), adenovirus vectors (e.g., Logan et al., *PNAS. USA*, 81:3655–3659 (1984); ones et al., *Cell*, 17:683–689 (1979); Berkner, *Biotechniques*, 6:616–626 (1988); Cotten et al., *PNAS, USA*, 89:6094–6098 (1992); Graham et al., *Meth. Mol. Biol.*, 7:109–127 (1991)), adeno-associated virus vectors, retrovirus vectors (see, e.g., U.S. Pat. Nos. 4,405,712 and 4,650,764), and the like. Especially preferred viral vectors are the adenovirus and retroviral vectors.

For example, in one embodiment of the present invention, adenovirus-transferrin/polylysine-DNA (TfAdpl-DNA) vector complexes (Wagner et al., *PNAS. USA*, 89:6099–6103 (1992); Curiel et al., *Hum. Gene Ther.*, 3:147–154 (1992); Gao et al., *Hum. Gene Ther.*, 4:14–24 (1993)) are employed to transduce mammalian cells with heterologous SBP nucleic acid. Any of the plasmid expression vectors described herein may be employed in a TfAdpl-DNA complex.

As used herein, "retroviral vector" refers to the well-known gene transfer plasmids that have an expression cassette encoding an heterologous gene residing between two retroviral LTRs. Retroviral vectors typically contain appropriate packaging signals that enable the retroviral vector, or RNA transcribed using the retroviral vector as a template, to be packaged into a viral virion in an appropriate packaging cell line (see, e.g., U.S. Pat. No. 4,650,764).

Suitable retroviral vectors for use herein are described, for example, in U.S. Pat. No. 5,252,479, and in WIPO publications WO 92/07573, WO 90/06997, WO 89/05345, WO 92/05266 and WO 92/14829, incorporated herein by reference, which provide a description of methods for efficiently introducing nucleic acids into human cells using such retroviral vectors. Other retroviral vectors include, for example, the mouse mammary tumor virus vectors (e.g., Shackleford et al., *PNAS. USA*, 85:9655–9659 (1988)), and the like.

In accordance with yet another embodiment of the present invention, there are provided anti-SBP antibodies having specific reactivity with an SBP polypeptides of the present invention. Active fragments of antibodies are encompassed within the definition of "antibody". Invention antibodies can be produced by methods known in the art using invention polypeptides, proteins or portions thereof as antigens. For example, polyclonal and monoclonal antibodies can be produced by methods well known in the art, as described, for example, in Harlow and Lane, *Antibodies: A Laboratory Manual* (Cold Spring Harbor Laboratory (1988)), which is incorporated herein by reference. Invention polypeptides can be used as immunogens in generating such antibodies. Alternatively, synthetic peptides can be prepared (using commercially available synthesizers) and used as immunogens. Amino acid sequences can be analyzed by methods well known in the art to determine whether they encode hydrophobic or hydrophilic domains of the corresponding polypeptide. Altered antibodies such as chimeric, humanized, CDR-grafted or bifunctional antibodies can also be produced by methods well known in the art. Such antibodies can also be produced by hybridoma, chemical synthesis or recombinant methods described, for example, in Sambrook et al., supra., and Harlow and Lane, supra. Both anti-peptide and anti-fusion protein antibodies can be used. (see, for example, Bahouth et al., *Trends Pharmacol. Sci.* 12:338 (1991); Ausubel et al., *Current Protocols in Molecular Biology* (John Wiley and Sons, NY (1989) which are incorporated herein by reference).

Antibody so produced can be used, inter alia, in diagnostic methods and systems to detect the level of SBP present in a mammalian, preferably human, body sample, such as tissue or vascular fluid. Such antibodies can also be used for the immunoaffinity or affinity chromatography purification of the invention SBP. In addition, methods are contemplated herein for detecting the presence of an invention SBP protein either within a cell, or on the surface of a cell, comprising contacting the cell with an antibody that specifically binds to SBP polypeptides, under conditions permitting binding of the antibody to the SBP polypeptides, detecting the presence of the antibody bound to the SBP polypeptide, and thereby detecting the presence of invention polypeptides on the surface of the cell. With respect to the detection of such polypeptides, the antibodies can be used for in vitro diagnostic or in vivo imaging methods.

Immunological procedures useful for in vitro detection of target SBP polypeptides in a sample include immunoassays that employ a detectable antibody. Such immunoassays include, for example, ELISA, Pandex microfluorimetric assay, agglutination assays, flow cytometry, serum diagnostic assays and immunohistochemical staining procedures which are well known in the art. An antibody can be made detectable by various means well known in the art. For example, a detectable marker can be directly or indirectly attached to the antibody. Useful markers include, for example, radionucleotides, enzymes, fluorogens, chromogens and chemiluminescent labels.

Invention anti-SBP antibodies are contemplated for use herein to modulate the activity of the SBP polypeptide in living animals, in humans, or in biological tissues or fluids isolated therefrom. The term "modulate" refers to a compound's ability to increase (e.g., via an agonist) or inhibit (e.g., via an antagonist) the biological activity of an invention SBP protein, such as the schwannomin-binding or ribosomal DNA-binding activity of an SBP. Accordingly, compositions comprising a carrier and an amount of an antibody having specificity for SBP polypeptides effective to block naturally occurring ligands or other SBP-binding proteins (e.g., schwannomin, and the like) from binding to invention SBP polypeptides are contemplated herein. For example, a monoclonal antibody directed to an epitope of an invention SBP polypeptide including an amino acid sequence set forth in SEQ ID NOs:2, 4, 6, 8 or 10, can be useful for this purpose.

The present invention further provides transgenic non-human mammals that are capable of expressing exogenous nucleic acids encoding SBP polypeptides. As employed herein, the phrase "exogenous nucleic acid" refers to nucleic acid sequence which is not native to the host, or which is present in the host in other than its native environment (e.g., as part of a genetically engineered DNA construct). In addition to naturally occurring levels of SBP, invention SBPs can either be overexpressed or underexpressed (such as in the well-known knock-out transgenics) in transgenic mammals.

Also provided are transgenic non-human mammals capable of expressing nucleic acids encoding SBP polypeptides so mutated as to be incapable of normal activity, i.e., do not express native SBP. The present invention also provides transgenic non-human mammals having a genome comprising antisense nucleic acids complementary to nucleic acids encoding SBP polypeptides, placed so as to be transcribed into antisense mRNA complementary to mRNA encoding SBP polypeptides, which hybridizes to the mRNA and, thereby, reduces the translation thereof. The nucleic acid may additionally comprise an inducible promoter and/or tissue specific regulatory elements, so that expression can be induced, or restricted to specific cell types. Examples of nucleic acids are DNA or cDNA having a coding sequence substantially the same as the coding sequence shown in SEQ ID NOs:1, 3, 5, 7 and 9. An example of a non-human transgenic mammal is a transgenic mouse. Examples of tissue specificity-determining elements are the metallothionein promoter and the L7 promoter.

Animal model systems which elucidate the physiological and behavioral roles of SBP polypeptides are also provided, and are produced by creating transgenic animals in which the expression of the SBP polypeptide is altered using a variety of techniques. Examples of such techniques include the insertion of normal or mutant versions of nucleic acids encoding an SBP polypeptide by microinjection, retroviral infection or other means well known to those skilled in the art, into appropriate fertilized embryos to produce a transgenic animal. (See, for example, Hogan et al., *Manipulating the Mouse Embryo: A Laboratory Manual* (Cold Spring Harbor Laboratory, (1986)).

Also contemplated herein, is the use of homologous recombination of mutant or normal versions of SBP genes with the native gene locus in transgenic animals, to alter the regulation of expression or the structure of SBP polypeptides (see, Capecchi et al., *Science* 244:1288 (1989); Zimmer et al., *Nature* 338:150 (1989); which are incorporated herein by reference). Homologous recombination techniques are well known in the art. Homologous recombination replaces the native (endogenous) gene with a recombinant or mutated gene to produce an animal that cannot express native (endogenous) protein but can express, for example, a mutated protein which results in altered expression of SBP polypeptides.

In contrast to homologous recombination, microinjection adds genes to the host genome, without removing host genes. Microinjection can produce a transgenic animal that is capable of expressing both endogenous and exogenous SBP. Inducible promoters can be linked to the coding region of nucleic acids to provide a means to regulate expression of the transgene. Tissue specific regulatory elements can be linked to the coding region to permit tissue-specific expression of the transgene. Transgenic animal model systems are useful for in vivo screening of compounds for identification of specific ligands, i.e., agonists and antagonists, which activate or inhibit protein responses.

Invention nucleic acids, oligonucleotides (including antisense), vectors containing same, transformed host cells, polypeptides and combinations thereof, as well as antibodies of the present invention, can be used to screen compounds in vitro to determine whether a compound functions as a potential agonist or antagonist to invention polypeptides. These in vitro screening assays provide information regarding the function and activity of invention polypeptides, which can lead to the identification and design of compounds that are capable of specific interaction with one or more types of polypeptides, peptides or proteins.

Schwannomin is known to be a tumor suppressor protein. Tumor suppressor proteins generally are thought to have a function in signal transduction. Mutation results in loss of function whereupon a signal pathway that the suppressor protein regulates is left in the "on" position, which results in unregulated cell proliferation resulting in cancerous tumor formation. Nearly all tumor suppressors regulate cell division, and proliferation, and may have involvement in biochemical pathways of development and the cell cycle.

Through the identification of the invention binding proteins of schwannomin, it has been discovered that schwannomin has roles in the regulation of transcription and translation. It has also been found that both the invention schwannomin-binding-protein set forth in SEQ ID NO:6 and schwannomin are involved in the transcriptional regulation of ribosomal DNA. It has also been found that invention SBPs comprising SEQ ID Nos:2 and 10 appear to have roles in the regulation of transcription, while the invention SBP set forth in SEQ ID NO:4 is chiefly involved in the regulation of translation.

The functions of the invention schwannomin binding proteins support the role of both schwannomin and the invention SBPs in cellular pathways that effect cell division and proliferation and also provide targets for treating a broad variety of cancer pathologies, such as, gliomas, carcinomas, sarcomas, melanomas, hamartomas and the like. In certain aspects of the invention, invention SBPs, agonist or antagonists thereto, are used to treat brain tumors, such as gliomas, schwannomas, meningiomas, ependymomas, and the like.

Thus, in accordance with still another embodiment of the present invention, there are provided methods for identifying compounds which bind to SBP polypeptides. The invention proteins may be employed in a competitive binding assay. Such an assay can accommodate the rapid screening of a large number of compounds to determine which compounds, if any, are capable of binding to SBPs. Subsequently, more detailed assays can be carried out with those compounds found to bind, to further determine whether such compounds act as modulators, agonists or antagonists of invention SBP proteins. Compounds that bind to and/or modulate invention SBPs can be used to treat a variety of pathologies mediated by invention SBPs. Such pathologies include, for example, schwannomas, meningiomas, ependymomas, cataracts, retinal disorders such as hamartomas, and the like.

In another embodiment of the invention, there is provided a bioassay for identifying compounds which modulate the activity of invention SBP polypeptides. According to this method, invention polypeptides are contacted with an "unknown" or test substance (in the presence of a reporter gene construct when antagonist activity is tested), the activity of the polypeptide is monitored subsequent to the contact with the "unknown" or test substance, and those substances which cause the reporter gene construct to be expressed are identified as functional ligands for SBP polypeptides.

In accordance with another embodiment of the present invention, transformed host cells that recombinantly express invention polypeptides can be contacted with a test compound, and the modulating effect(s) thereof can then be evaluated by comparing the SBP-mediated response (e.g., via reporter gene expression) in the presence and absence of test compound, or by comparing the response of test cells or control cells (i.e., cells that do not express SBP polypeptides), to the presence of the compound.

As used herein, a compound or a signal that "modulates the activity" of invention polypeptides refers to a compound or a signal that alters the activity of SBP polypeptides so that the activity of the invention polypeptide is different in the presence of the compound or signal than in the absence of the compound or signal. In particular, such compounds or signals include agonists and antagonists. An agonist encompasses a compound or a signal that activates SBP protein expression. Alternatively, an antagonist includes a compound or signal that interferes with SBP expression. Typically, the effect of an antagonist is observed as a blocking of agonist-induced protein activation. Antagonists include competitive and non-competitive antagonists. A competitive antagonist (or competitive blocker) interacts with or near the site specific for agonist binding. A non-competitive antagonist or blocker inactivates the function of the polypeptide by interacting with a site other than the agonist interaction site.

As understood by those of skill in the art, assay methods for identifying compounds that modulate SBP activity generally require comparison to a control. One type of a "control" is a cell or culture that is treated substantially the same as the test cell or test culture exposed to the compound, with the distinction that the "control" cell or culture is not exposed to the compound. For example, in methods that use voltage clamp electrophysiological procedures, the same cell can be tested in the presence or absence of compound, by merely changing the external solution bathing the cell. Another type of "control" cell or culture may be a cell or culture that is identical to the transfected cells, with the exception that the "control" cell or culture do not express native proteins. Accordingly, the response of the transfected cell to compound is compared to the response (or lack thereof) of the "control" cell or culture to the same compound under the same reaction conditions.

In yet another embodiment of the present invention, the activation of SBP polypeptides can be modulated by contacting the polypeptides with an effective amount of at least one compound identified by the above-described bioassays.

In accordance with another embodiment of the present invention, there are provided methods for diagnosing cancer, said method comprising:

detecting, in said subject, a defective sequence or mutant of SEQ ID NOs:1, 3, 5, 7 and 9.

In accordance with another embodiment of the present invention, there are provided diagnostic systems, preferably in kit form, comprising at least one invention nucleic acid in a suitable packaging material. The diagnostic nucleic acids are derived from the SBP-encoding nucleic acids described herein. In one embodiment, for example, the diagnostic nucleic acids are derived from any of SEQ ID NOs:1, 3, 5, 7 and 9. Invention diagnostic systems are useful for assaying for the presence or absence of nucleic acid encoding SBP in either genomic DNA or in transcribed nucleic acid (such as mRNA or cDNA) encoding SBP.

A suitable diagnostic system includes at least one invention nucleic acid, preferably two or more invention nucleic acids, as a separately packaged chemical reagent(s) in an amount sufficient for at least one assay. Instructions for use of the packaged reagent are also typically included. Those of skill in the art can readily incorporate invention nucleic acid probes and/or primers into kit form in combination with appropriate buffers and solutions for the practice of the invention methods as described herein.

As employed herein, the phrase "packaging material" refers to one or more physical structures used to house the contents of the kit, such as invention nucleic acid probes or primers, and the like. The packaging material is constructed by well known methods, preferably to provide a sterile, contaminant-free environment. The packaging material has a label which indicates that the invention nucleic acids can be used for detecting a particular sequence encoding SBP including the nucleotide sequences set forth in SEQ ID NOs:1, 3, 5, 7 and 9 or mutations or deletions therein, thereby diagnosing the presence of, or a predisposition for, cancer. In addition, the packaging material contains instructions indicating how the materials within the kit are employed both to detect a particular sequence and diagnose the presence of, or a predisposition for, cancer.

The packaging materials employed herein in relation to diagnostic systems are those customarily utilized in nucleic acid-based diagnostic systems. As used herein, the term "package" refers to a solid matrix or material such as glass, plastic, paper, foil, and the like, capable of holding within fixed limits an isolated nucleic acid, oligonucleotide, or primer of the present invention. Thus, for example, a package can be a glass vial used to contain milligram quantities of a contemplated nucleic acid, oligonucleotide or primer, or it can be a microtiter plate well to which microgram quantities of a contemplated nucleic acid probe have been operatively affixed.

"Instructions for use" typically include a tangible expression describing the reagent concentration or at least one assay method parameter, such as the relative amounts of reagent and sample to be admixed, maintenance time periods for reagent/sample admixtures, temperature, buffer conditions, and the like.

All U.S. patents and all publications mentioned herein are incorporated in their entirety by reference thereto. The invention will now be described in greater detail by reference to the following non-limiting examples.

Materials and Methods

Unless otherwise stated, the present invention was performed using standard procedures, as described, for example in Maniatis et al., *Molecular Cloning: A Laboratory Manual*, Cold Spring Harbor Laboratory Press, Cold Spring Harbor, N.Y., USA (1982); Sambrook et al., *Molecular Cloning: A Laboratory Manual* (2 ed.), Cold Spring Harbor Laboratory Press, Cold Spring Harbor, N.Y., USA (1989); Davis et al., *Basic Methods in Molecular Biology*, Elsevier Science Publishing, Inc., New York, USA (1986); or *Methods in Enzymology: Guide to Molecular Cloning Techniques* Vol.152, S. L. Berger and A. R. Kimmerl Eds., Academic Press Inc., San Diego, USA (1987)).

EXAMPLE 1

Identification of cDNA Encoding Schwannomin-Binding-Proteins

Using a plasmid that codes for the full-length schwannomin isoform 2 fused to the binding domain of the transcription factor GAL4 (pGBT9NF212), a human adult brain cDNA library cloned in GAL4 activation domain fusion vector pGAD10 and screened by the yeast two-hybrid method (Fields et al., 1989, *Nature* 340:245–246). A human adult brain cDNA library (Clontech) was cloned into a GAL4 activation domain vector pGAD10 (Clontech). Using the plasmid pGBT9NF212, encoding full-length schwannomin isoform 2 fused to the GAL4 binding domain (Clontech), the yeast two-hybrid assay was carried out. A plasmid encoding βII-spectrin, pGAD10Sp, was purified and retransformed with pGBT9NF212, pGBT9NF2, encoding schwannomin isoform 1, or subclones of each. Yeast strain Y190 double-transformants were grown on SC media with leucine, tryptophane, and histidine dropped out, and with 25 mM 3-amino-1,2,4-triazole and 2% glucose (Poullet and Tamanio, (1995)). β-Galactosidase production was assayed by incubating freeze-fractured colonies on nitrocellulose in Z-buffer (60 mM $Na_2HPO_4$, 40 mM $NaH_2PO_4$, 10 mM KCl, 1 mM $MgSO_4$, pH 7.0, 0.03 mM β-mercaptoethanol, and 2.5 μM X-gal) at 37° C. for 15 min to 8 hr.

A total of $6.6×10^6$ colonies were screened, of which eight were positive for β-galactosidase activity, evident by blue colonies. Plasmids were purified and cotransformed with pGBT9NF212 which reduced the number of transformants producing blue colonies to seven. Of these seven, one plasmid contained 846 bp of cDNA sequence encoding βII-spectrin (pGAD10Sp, residues 1716 to 1997), also known as fodrin. At least five of the clones encode novel Schwannomin-Binding-Proteins (SEQ ID NOs:1, 3, 5, 7 and 9).

EXAMPLE 2

Characterization of Schwannomin:βII-Spectrin Binding

To determine which domains of schwannomin are responsible for βII-spectrin binding, deletion constructs were generated containing N- and C-terminal, and α domain deletions of schwannomin and tested by the above-described two-hybrid method (FIG. 1). Schwannomin proteins with residues 400–547 deleted showed no interaction with βII-spectrin, whereas proteins with N-terminal and α domain deletions bound to βII-spectrin. Schwannomin proteins with deletions that interact indicate that spectrin binding requires residues within 469–547 of either schwannomin isoform (FIG. 1).

Figure 2:
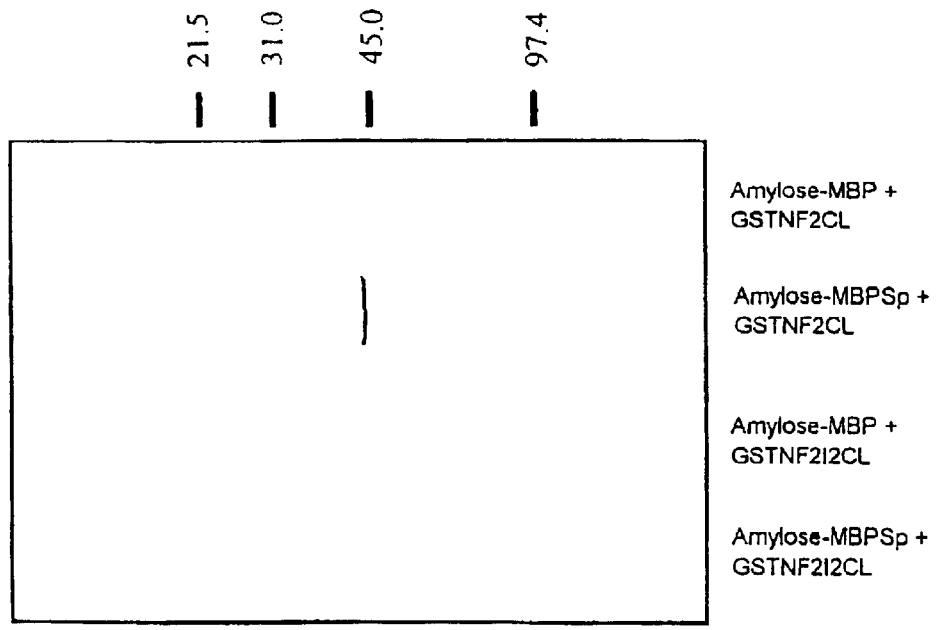
FIG. 2 shows in vitro tests of interaction between βII-spectrin and schwannomin as described in Example 3.

Regions necessary for binding of spectrin and schwannomin are within residues 469–547 of schwannomin and residues 1779–1884 of βII-spectrin. Of all the tested constructs, binding strength was greatest for the full-length schwannomin isoform 2, which was much greater than that for full-length isoform 1 (FIGS. 1 and 2). However, very short C-terminal constructs gave the inverse results between the isoforms, suggesting that the highly charged isoform 2 requires the α-helical and possibly the N-terminal domain to stabilize binding with βII-spectrin.

Strengths of interactions between βII-spectrin and schwannomin were also assessed using a semiquantitative liquid assay for β-galactosidase (Poullet and Tamanio, (1995)). β-galactosidase activities were stronger for the full-length schwannomin isoform 2 than for isoform 1 (FIG. 1). Among the deletion constructs, only those expressing schwannomin C-terminal domains demonstrated β-galactosidase activity. The shortest C-terminal domain constructs presented low levels of β-galactosidase activity, and unlike the full-length proteins, isoform 1 displayed greater activity than isoform 2. The results also indicate that proteins with N-terminal domain deletions presented greater β-galactosidase activities than shorter proteins with both N-terminal and α domains deleted.

The marked differences in binding affinities of βII-spectrin for different schwannomin isoforms suggests alternative splicing results in a charged C-terminal domain in schwannomin isoform 2 that greatly enhances the interaction. Similar observations have been made for protein 4.1, in which only isoforms containing 21 amino acids encoded by an alternatively spliced exon can bind spectrin (Discher et al., *J. Biol. Chem.* 268:7186–7195 (1993)). Affinity for βI-spectrin by protein 4.1 is further elevated by phosphorylation of tyrosine 418 (Subrahmanyam et al., *Proc. Natl. Acad. Sci. U.S.A.* 88:5222–5226 (1991)). Although this tyrosine is not conserved in schwannomin, phosphorylation of schwannomin has also been shown to affect protein binding (Takeshima et al., (1994)).

These data suggest a role for schwannomin in spectrin mediated signal transduction. βII-spectrin redistributes in response to extracellular singles such as thrombin-induced platelet aggregation, and cell-cell interaction in MDCK cells (Nelson et al., *J. Cell Biol.* 110:249–357 (1990) and Fox et al., *J. Biol. Chem.* 268:25973–25984 (1993)). Similar to spectrin, the actin cytoskeleton in addition to its structural function, is known to disassemble and redistribute rho-related proteins in response to extracellular signals. Transmembrane receptors that interact with the βII-spectrin binding protein ankyrin may communicate extracellular singles responsible for reorganization of spectrin. These include $Na^+,K^+$-ATPase in MDCK cells, the neural cell adhesion protein N-CAM, the tyrosine phosphatase CD45, and CD44. It is not presently known which of these proteins are expressed in Schwann cells.

Another tumor suppressor, the adenomatosis polypoposia coli (APC) protein, also interacts with cytoskeletal elements. Coimmunoprecipitation and two-hybrid studies showed that APC and E-cadherin, which mediates cell morphology and adhesion, compete for interaction with β-catenin (Rubinfeld et al., *Science* 262:1731–1734 (1993), Su et al., *Science* 262:1734–1737 (1993), and Hülsken et al., *J. Cell Biol.* 127:2061–2069 (1994)). Since spectrin forms a complex with E-cadherin (Tsukita et al., (1994)) and cell morphology and adhesion are strikingly altered in STS6T cells after treatment with NF2 antisense-nucleic acids (Huynh and Pulst (1996)), E-cadherin may be involved in schwannomin action.

EXAMPLE 3

In vitro Schwannomin:Spectrin Binding Assay

To confirm the results obtained by the two-hybrid method, the interaction between spectrin and the schwannomin C-terminal domain was verified in vitro. Amylose resin was saturated with a purified maltose binding protein (MBP) or MBP fused with βII-spectrin residues 1779–1992 (MBPSp). Segments of βII-spectrin were amplified by polymerase chain reaction and cloned in pMALC2 (New England BioLabs). MBP and MBP:βII-spectrin fusions (MBPSp) were expressed in *E coli* DH5α and purified using amylose resin (New England BioLabs). Residues 469–595 of schwannomin isoform 1 (NF2CL) and residues 469–590 of schwannomin isoform 2 (NF212CL) were expressed in DH5α as fusions to glutathione-S-transferase (GST) using pGEX-5X-1 (Pharmacia) and were purified using Sepharose 4B-glutathione (Pharmacia).

Purified MBP or MBP fusions were incubated with fresh amylose resin for 5 minutes at room temperature and 2.5 minutes at 4° C. in column buffer (20 mM Tris-HCl, pH 7.4, 200 mM NaCl, 1 mM EDTA, 2 μg/ml aprotinin, 0.5 mg/ml Perfabloc SC), and washed three times with binding buffer (160 mM NaCl, 2.5 mM $MgCl_2$, 1.5 mM $CaCl_2$, mM KCl, 50 mM hepes, pH 7.4, 1% Triton X-100, 2 μg/ml aprotinin, and 0.5 mg/ml Pefabloc SC). Saturated amylose resin was incubated with equivalent amounts of GSTNF2CL or GSTNF212CL for 20 min at 4° C. and washed three times with binding buffer. The quantities were normalized by conducting dot blots of serial dilutions detected with anti-GST antibody (Pharmacia). Western blot analysis was conducted as described using affinity purified rabbit anti-spectrin (Sigma S1515), and anti-schwannomin (Ab5990, recognizes C-terminal domain) polyclonal antibodies (Huynh and Pulst (1996)).

Purified MBPSp was recognized by a spectrin antibody which revealed a single band of size consistent with the predicted molecular weight of 63.7 kDa. Glutathione-S-transferase (GST) fusions were purified with the C-terminal domain of schwannomin isoform 1 (GSTNF2CL, schwannomin residues 469–595) or isoform 2 (GSTNF212CI, schwannomin residues 469–590). When the MBPSp-amylose resin was incubated with schwannomin-GST fusion proteins, the proteins eluted from the washed resin were recognized by an anti-schwannomin antibody (Ab5990). The bands observed had apparent molecular weights consistent with the predicted 40.0 kDa for the isoform 1 C-terminal domain GST fusion, or 39.4 kDa for that of isoform 2 (FIG. 2). When resin saturated with MBP protein alone was incubated with these GST-schwannomin fusion proteins, no eluted proteins were recognized by Ab5990 (FIG. 2). These results were reproducible. Assays using MBP fused with β-spectrin residues 1885–1967 or residues 1885–1992 yielded no evidence of interaction with GST-schwannomin fusions. Therefore, interaction between spectrin and schwannomin requires spectrin residues within 1779–1884, within βII-spectrin repeat 15.

EXAMPLE 4

Immunohistochemical Staining Assay

To determine the distribution of spectrin in the target tissues involved in the NF2 phenotype, antibodies to spectrin and schwannomin were used to demonstrate that these proteins occurred in the same cells, and that spectrin was a target for schwannomin binding in vivo. Immunohistochemical staining was conducted as described previously (Sainz et al., (1994)). Staining was accomplished with 1:2,000 dilution of rabbit anti-spectrin antibody (Sigma S1515), 20 μg/ml of Ab5990, or 1:2,000 dilution of rabbit preserum incubated with tissue sections overnight at 4° C. Primary antibodies were detected using the Vector ABC elite Peroxidase Kit (Vector), enhanced by DAB enhancer, and visualized with diaminobenzidine (DAB) (Biomeda). Sections were counterstained using aqueous hematoxylin (Xymed). Absorption controls were conducted using Ab5990 preabsorbed with peptide antigen at 100 μM for hr at room temperature.

As previously shown (Sainz et al., (1994), and Huynh and Pulst (1996)), schwannomin expression was detected in normal Schwann cells, but not in schwannomas containing NF2 mutations. Unlike schwannomin, spectrin staining was detected in both normal eighth nerve and vestibular schwannomas.

In the retina (one of the tissues involved in the non-tumor features of NF2), schwannomin and spectrin expression was restricted to specific retinal cell types. Both proteins were detected in rods and cones, but little expression was seen in neurons of other retinal layers. The unpigmented epithelium of the ciliary body and all pigment epithelia expressed both spectrin and schwannomin. Staining of both proteins was also seen in corneal epithelium.

The NF2 gene is abundantly expressed in muscle tissue and spectrin has a distinct localization to the I-bands in striated muscle (Nelson and Lazarides, *Biochem.* 81:3292–3296 (1984)). Nelson and Lazarides, (1984), describes the location of spectrin in striated muscle, adjacent to Z-lines which occur within I-bands. This provided the opportunity to test whether schwannomin was localized to the same structures as spectrin. Longitudinal sections of human striated muscle were prepared and adjacent sections were stained with spectrin and schwannomin antibodies. Clear colocalization of schwannomin and spectrin with the I-bands was observed.

The specific tissue distribution of spectrin and schwannomin suggests that their interaction may be significant not only for tumorigenesis, but may also explain the non-tumor features of NF2. Cataracts are common in NF2 patients (Mautner et al., (1996)) and may involve spectrin. Degradation of the spectrin skeleton is typically seen in a rat cataract model. In the retinal pigment epithelium (RPE), one function of the βII-spectrin-ankyrin complex is the positioning of $Na^+,K^+$-ATPase in the apical membrane. Interestingly, signals received by cadherins also affect $Na^+,K^+$-ATPase distribution and stimulate assembly of the spectrin skeleton in RPE (Marrs, et al., *J. Cell Biol.* 129:507–519 (1995)). Colocalized staining of spectrin and schwannomin in the RPE indicates that both may have a role in the development of retinal hamartomas in NF2 patients (Mautner, et al. (1996)). It is striking that RPE hamartomas (congenital hypertrophy of the RPE), are also common in patients with APC gene mutation (Kasner et al., *Retina* 12:35–42 (1992) and Santos et al., *Retina* 14:6–9 (1994)) and may point to common final pathways for APC and schwannomin.

EXAMPLE 5

Colocalization in STS26T Cells

Although muscle cells have the advantage of a spatially dispersed cytoskeletal organization which allows localization of proteins to easily identifiable structures, muscle pathology is not part of the NF2 phenotype. Therefore, colocalization in STS26T cells was examined. These cells have a Schwann-like phenotype, including spindle shape, S100 immunoreactivity, and exhibit loss of cell attachment and increased proliferation when schwannomin expression is reduced. Schwann-like STS26T cells derived from a human malignant schwannoma were grown in DMEM+10% FBS +1× antimycotic agent for 72 hr at 37%C. Cells were stripped using 0.5% trypsin and 1 mM EDTA, washed with culture media, and distributed 5,000–10,000 cells per well in 4-well sides. Cells were double-labeled for immunofluorescence as previously described (Huynh and Pulst (1996)), by incubating in 20 μg/ml of Ab5990 and 1:40 dilution of mouse monoclonal anti-spectrin (Sigma SB-SP1, S3396), or in rabbit preimmune serum, for one hour at room temperature. Following three washes with cold DPBS, cells were incubated with TRITC conjugated affinity purified goat anti-rabbit IgG (Sigma, T6778) and FITC conjugated affinity purified goat anti-mouse IgG (Sigma F3008) for one hour at room temperature, washed four times in cold DPBS, and mounted.

Fluorescence microscopy was preformed using a Zeiss LSM 210 confocal microscope. FITC visualization was achieved using a 488 nm argon laser with a 488 nm/525 nm excitation/emission filter set, and a 520 nm barrier filter. Rhodamine visualization utilized a 543 nm HeNe laser with a 540 nm/580 nm excitation/emission filter set, and a 590 nm barrier filter. Photographs were obtained using a Sony video printer (UP-5200MD).

By confocal microscopy, staining for spectrin and schwannomin was colocalized in the cytoplasm with a distribution similar to that previously observed for spectrin in other cell types (Nelson and Veshnock, Cell Biol. 103:1751–1765 (1986)). In addition, dividing STS26T cells strongly stained in the nucleolus for both schwannomin and spectrin.

In addition to cytoplasmic colocalization, both βII-Spectrin and schwannomin colocalized to the nucleoli of dividing STS26T cells. Interestingly, protein 4.1, which has homologies to schwannomin, has also been detected in the nucleus (Carcer et al., Biochem. J. 312:871–877 (1991)). Transport could be mediated by possible nuclear targeting signal sequences in βII-spectrin and schwannomin (Jans, FASEB J. 8:841–7 (1994)). Another human tumor suppressor protein, the Rb protein, is transported to the nucleolus, where it down-regulates ribosomal RNA production by binding RNA polymerase I transcription factor UBF (Cavanaugh et al., Nature 374:177–180 (1995)). There is strong evidence that β-catenin is also transported to the nucleus in Xenopus (Funayama, et al., J. Cell Biol. 128:959–968 (1995)). Similarities between APC and schwannomin, and overlap in patient phenotypes suggest pathways that are linked and similar to one another, and may have functions like Rb.

While the invention has been described in detail with reference to certain preferred embodiments thereof, it will be understood that modifications and variations are within the spirit and scope of that which is described and claimed.

Summary of Sequences

SEQ ID NO:1 is a cDNA (and the deduced amino acid sequence) encoding a schwannomin-binding fragment of a human SBP of the present invention.

SEQ ID NO:2 is the deduced amino acid sequence of a schwannomin-binding, carboxy terminal fragment of a human SBP protein of the present invention encoded by SEQ ID NO:1.

SEQ ID NO:3 is a cDNA (and the deduced amino acid sequence) encoding a human SBP polypeptide of the present invention.

SEQ ID NO:4 is the deduced amino acid sequence of a human SBP protein of the present invention encoded by SEQ ID NO:3.

SEQ ID NO:5 is a cDNA (and the deduced amino acid sequence) encoding a human SBP polypeptide of the present invention.

SEQ ID NO:6 is the deduced amino acid sequence of a human SBP protein of the present invention encoded by SEQ ID NO:5.

SEQ ID NO:7 is a cDNA (and the deduced amino acid sequence) encoding a schwannomin-binding fragment of a human SBP polypeptide of the present invention.

SEQ ID NO:8 is the deduced amino acid sequence of a schwannomin-binding, internal fragment of a human SBP protein of the present invention encoded by SEQ ID NO:7.

SEQ ID NO:9 is a cDNA (and the deduced amino acid sequence) encoding a human SBP polypeptide of the present invention.

SEQ ID NO:10 is the deduced amino acid sequence of a schwannomin-binding, carboxy terminal fragment of a human SBP protein encoded by SEQ ID NO:9.

What is claimed is:

1. An isolated SBP comprising the same amino acid sequence as set forth in SEQ ID NO: 6.

2. An isolated Schwannomin-Binding Protein (SBP), wherein said SBP is encoded by a nucleotide sequence comprising the same nucleotide sequence as set forth in SEQ ID NO: 5.

3. An isolated Schwannomin-Binding Protein (SBP), wherein said SBP is encoded by a nucleotide sequence consisting of the same nucleotide sequence as set forth in SEQ ID NO: 12.

* * * * *